(12) United States Patent
DeBelser et al.

(10) Patent No.: US 8,694,331 B2
(45) Date of Patent: Apr. 8, 2014

(54) SOFTWARE FEATURES FOR MEDICAL INFUSION PUMP

(75) Inventors: David DeBelser, Plymouth, MN (US); Larry R. Zalesky, Milaca, MN (US); Kevin Sean Kopp, St. Paul, MN (US); Clinton Robert Hetchler, Minnetonka, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 640 days.

(21) Appl. No.: 12/416,603

(22) Filed: Apr. 1, 2009

(65) Prior Publication Data

US 2009/0270833 A1 Oct. 29, 2009

Related U.S. Application Data

(60) Provisional application No. 61/041,490, filed on Apr. 1, 2008.

(51) Int. Cl.
*G06Q 10/00* (2012.01)
*A61M 1/00* (2006.01)

(52) U.S. Cl.
USPC ............................................... 705/2; 604/51

(58) Field of Classification Search
USPC .......................................................... 705/2
See application file for complete search history.

(56) References Cited

U.S. PATENT DOCUMENTS

| | | | |
|---|---|---|---|
| 5,292,306 A * | 3/1994 | Wynkoop et al. | 604/505 |
| 5,531,697 A | 7/1996 | Olsen et al. | |
| 5,695,473 A | 12/1997 | Olsen | |
| 5,935,106 A * | 8/1999 | Olsen | 604/153 |
| 6,475,180 B2 * | 11/2002 | Peterson et al. | 604/65 |
| 7,935,105 B2 | 5/2011 | Miller et al. | |
| 8,034,026 B2 * | 10/2011 | Grant et al. | 604/121 |
| 2003/0140929 A1 | 7/2003 | Wilkes et al. | |
| 2004/0167465 A1 | 8/2004 | Mihai et al. | |
| 2005/0242928 A1 | 11/2005 | Kirkeby | |
| 2005/0246416 A1 | 11/2005 | Blomquist | |
| 2006/0031094 A1 | 2/2006 | Cohen et al. | |
| 2008/0033360 A1 | 2/2008 | Evans et al. | |
| 2008/0033361 A1 | 2/2008 | Evans et al. | |
| 2008/0033402 A1 | 2/2008 | Blomquist | |

(Continued)

FOREIGN PATENT DOCUMENTS

| | | |
|---|---|---|
| WO | WO9636923 | 11/1996 |
| WO | WO2005101279 | 10/2005 |

(Continued)

OTHER PUBLICATIONS

International Preliminary Report dated Oct. 10, 2010 for PCT Application No. PCT/US2009/039181 filed Apr. 1, 2009.

(Continued)

*Primary Examiner* — Hiep V Nguyen
(74) *Attorney, Agent, or Firm* — Patterson Thuente Pedersen, P.A.

(57) ABSTRACT

Various software features useable in a medical infusion pump are disclosed. In certain aspects, localized alarm and message handling systems are disclosed. In other aspects, variable intensity alarms are disclosed. In further aspects, cost tracking systems and methods for medical infusion pumps are disclosed. In still further aspects, methods and systems implementing a variable delay of pressure decay in a medical infusion pump are disclosed. In other aspects, methods and systems implementing a timed intermittent bolus by pressure are disclosed.

63 Claims, 21 Drawing Sheets

(56) References Cited

U.S. PATENT DOCUMENTS

| | | |
|---|---|---|
| 2008/0033749 A1 | 2/2008 | Blomquist |
| 2008/0034323 A1 | 2/2008 | Blomquist |
| 2008/0126969 A1 | 5/2008 | Blomquist |
| 2010/0262078 A1 | 10/2010 | Blomquist |
| 2013/0012879 A1 | 1/2013 | DeBelser |
| 2013/0013338 A1 | 1/2013 | DeBelser |

FOREIGN PATENT DOCUMENTS

| | | |
|---|---|---|
| WO | WO2005118028 | 12/2005 |
| WO | WO2006026270 | 3/2006 |
| WO | WO2008016621 | 2/2008 |
| WO | WO2008019013 | 2/2008 |

OTHER PUBLICATIONS

Technical Manual CADD-Legacy Ambulatory Infusion Pumps. Smiths Industries. Issue Date Jan. 2000.

European Search Report for European Application No. EP10189581 dated Jun. 17, 2013.

Chinese First Office Action for Chinese Application No. 200980121203.3 dated May 9, 2013. Brief Information of the Office Action in English.

European Search Report for European Application No. EP10189582 dated Aug. 22, 2013.

Application and File History for U.S. Appl. No. 13/619,833, filed Sep. 14, 2012, inventor DeBelser.

Application and File History for U.S. Appl. No. 13/619,904, filed Sep. 14, 2012, inventor DeBelser.

Australian Patent Examination Report No. 1 for Australian Application No. 2010236090 dated Dec. 4, 2013.

Australian Patent Examination Report No. 1 for Australian Application No. 2010236096 dated Dec. 4, 2013.

Australian Patent Examination Report No. 1 for Australian Application No. 2010236092 dated Dec. 4, 2013.

Chinese Office Action for Chinese Application No. 2009801212203.3 dated Jan. 8, 2014. English translation not available.

Chinese Office Action for Chinese Application No. 201110299442.7 dated Sep. 17, 2013. English Summary of the Examination Opinions attached.

* cited by examiner

```
Pump ID, Patient ID, Event Type, Time, Description
Pump 1; John Doe, Set Change, 01/01/01 12:00, New Infusion Set
Pump 1; John Doe, Cassette Change, 01/01/01 12:00, Change of Pump Cassette (Drug)
Pump 1; John Doe, Pump Program, 01/01/01 12:01, Program Pump (Drug, 25 mL/Hr)
Pump 1; John Doe, Pump Program, 01/01/01 12:01, Cancel Pump Program (Exception)
Pump 1; John Doe, Pump Program, 01/01/01 12:01, Program Pump (Drug, 50 mL/Hr)
Pump 1; John Doe, Drug Delivery, 01/01/01 12:02, Initiate Drug Delivery (Drug)
Pump 1; John Doe, Drug Delivery, 01/01/01 12:02, Cease Drug Delivery (Drug)
Pump 1; John Doe, Drug Delivery, 01/01/01 12:02, Initiate Drug Delivery (Drug)
Pump 1; John Doe, Drug Delivery, 01/01/01 3:00, Soft Limit Reached (High)
Pump 1; John Doe, Drug Delivery, 01/01/01 5:00, Complete Drug Delivery (250mL)
Pump 1; John Doe, Operation, 01/01/01 5:00, Cease Operation (4 Hours, 58 Minutes)
Pump 1; John Doe, Battery, 01/01/01 5:00, Battery Remaining 15%
Pump 1; John Doe, Battery, 01/01/01 5:15, Change Battery
Pump 2; Jane Doe, ...
```

```
Message Type;  Target Individuals;  Communication Type; Severity
Drug Alarm; Pharmacists; Nearing End of Drug Supply; Low
Drug Alarm; Pharmacists; End of Drug Supply; High
Notification Message; Patient, Nurses; Blocked Infusion Line; Low
Exception; All Registered Recipients; Pump Exception – Shutdown; High
Drug Alarm; Pharmacists; Frequent Delivery Limit Reached; Medium
Drug Alarm; Nurses; Soft Limit Reached in Pump; Low
Drug Alarm; All Registered Logins; Patient Disabled Pump; Medium
Patient Alert; Primary Physician (Dr. One); Patient Assistance Requested; Medium
...
```

| ID | Name | Class | Contact Method 1 | Contact Method 2 |
|---|---|---|---|---|
| 1 | Dr. One | Physician | Pager: (612)123-4567 | Cell: (612)987-6543 |
| 2 | Dr. Two | Physician | Cell: (999)321-4321 | Email: drtwo@email.com |
| 3 | Nurse Three | Nurse | Pager: (111)222-3333 | Email: nursethree@email.com |
| 4 | Nurse Four | Nurse | Text: (222)333-4444 | RSS |
| 5 | Nurse Five | Nurse | Text: (222)333-4444 | Pump Alarm |
| 6 | Pharm | Pharmacist | Phone: (333)444-5555 | Email: pharm@email.com |
| 7 | Pharm | Pharmacist | Phone: (444)555-6666 | Email: pharm2@email.com |
| 8 | Patient | Patient | Pump Alarm | Room Phone: 01234 |
| 9 | Clinician 1 | Clinician | Pump Alarm | Nurse's Station: 09876 |
| ... | | | | |

SOFTWARE FEATURES FOR MEDICAL INFUSION PUMP

CROSS-REFERENCE TO RELATED APPLICATIONS

The present application claims priority to U.S. Provisional Patent Application No. 61/041,490, filed Apr. 1, 2008, the disclosure of which is hereby incorporated by reference in its entirety.

TECHNICAL FIELD

The present disclosure relates to use of medical infusion pumps. In particular, the present disclosure relates to software useable in conjunction with a medical infusion pump.

BACKGROUND

Patients at hospitals and other care centers regularly require controlled drug intake as a part of the patient's prescribed therapy. One form of controlled drug intake is accomplished by infusing fluidic drugs with a medical infusion pump.

Medical infusion pumps, in general, provide regulated drug delivery to a patient. These pumps are used to deliver a selected drug or other therapeutic agent to a patient at a predetermined rate that is programmed into the pump. Programming and managing medical infusion pumps can be difficult and cumbersome. This can be due to the fact that a single pump can be programmed for delivering different fluids in different therapies and in different locations within a hospital. Programming fluid delivery rates can be difficult because maximum or minimum delivery rates can vary based on the patient, the fluid to be delivered, or certain conditions surrounding the pump.

Medical infusion pumps are often configured to track events occurring within the pumps, and to generate messages related to pump operation, such as describing current status and operational programming. When programmed incorrectly or operating outside of the bounds of current operational programming, the medical infusion pumps may also generate a number of types of alarms of differing severity. Managing these alarms, messages, and other and status indicators can be difficult for a variety of reasons. For example, to ensure that a qualified individual is notified of the existence of an alarm, alarms may be broadcast to a number of redundant individuals, causing a large volume of unnecessary alarm notifications. The generated alarms generally attract the most responsive individuals as opposed to those individuals best qualified to react to the alarms.

SUMMARY

In a first aspect, a method of directing messages to individuals is disclosed. The method includes associating one or more individuals with a message generated by a medical infusion pump. The method further includes following occurrence of the message in the medical infusion pump, communicating the message to the one or more individuals.

In a second aspect, a medical infusion pump is disclosed. The medical infusion pump includes a pump mechanism, a memory, and a programmable circuit arranged to control the pump mechanism and operatively connected to the memory. The programmable circuit is programmed to associate one or more individuals with a message generated by a medical infusion pump. The programmable circuit is also programmed to, following occurrence of the message in the medical infusion pump, communicate the message to the one or more individuals.

In a third aspect, a system for directing messages from a medical infusion pump to one or more individuals is disclosed. The system includes a medical infusion pump and a computing system communicatively connected to the medical infusion pump. The system is arranged to execute program instructions to associate one or more individuals with a message generated by a medical infusion pump, and, following occurrence of the message in the medical infusion pump, communicate the message to the one or more individuals.

In a fourth aspect, a method of tracking cost parameters relating to a medical infusion pump is disclosed. The method includes detecting in a medical infusion pump one or more cost-incurring events, each of the cost-incurring events relating to use of the medical infusion pump by a patient. The method also includes storing a history of the cost-incurring events in a memory, and generating a cost summary based on use of the medical infusion pump as recorded in the history of cost-incurring events.

In a fifth aspect, a medical infusion pump is disclosed. The medical infusion pump includes a pump mechanism, a memory, and a programmable circuit arranged to control the pump mechanism and operatively connected to the memory. The programmable circuit is programmed to detect in a medical infusion pump one or more cost-incurring events, each of the cost-incurring events relating to use of the medical infusion pump by a patient. The programmable circuit is further programmed to store a history of the cost-incurring events in the memory, and generate a cost summary based on use of the medical infusion pump as recorded in the history of cost-incurring events.

In a sixth aspect, a cost-tracking system for use with a medical infusion pump is disclosed. The cost tracking system includes a computing system and a medical infusion pump communicatively connected to the computing system. The medical infusion pump includes a pump mechanism, a memory, and a programmable circuit arranged to control the pump mechanism and operatively connected to the memory. The programmable circuit is programmed to detect in a medical infusion pump one or more cost-incurring events, each of the cost-incurring events relating to use of the medical infusion pump by a patient. The programmable circuit is further programmed to store a history of the cost-incurring events in the memory, and generate a cost summary based on use of the medical infusion pump as recorded in the history of cost-incurring events.

In a seventh aspect, a method of tracking activity in a medical infusion pump is disclosed. The method includes detecting in a medical infusion pump one or more cost-incurring events, each of the cost-incurring events relating to use of the medical infusion pump by a patient. The method also includes detecting in a medical infusion pump one or more corrective events, each of the corrective events relating to programming of the medical infusion pump by a caregiver. The method further includes storing an event log of the cost-incurring events and the corrective events in a memory of the medical infusion pump, and generating a cost summary based on at least a portion of the event log including one or more of the cost-incurring events.

In an eighth aspect, a method of assessing downstream pressure in a medical infusion pump is disclosed. The method includes determining a downstream pressure at the end of a pump stroke in a medical infusion pump, waiting a time period, and determining a downstream pressure at the end of the time period. The method also includes assessing the downstream pressure at the end of the time period, and, based on the assessing step, deciding whether to actuate a subsequent pump stroke.

In a ninth aspect, a medical infusion pump configured for management of fluid pressure decay is disclosed. The medical infusion pump includes a pump mechanism configured to actuate pump strokes to deliver fluids to a patient, a memory, and a programmable circuit arranged to control the pump mechanism and operatively connected to the memory. The programmable circuit is programmed to determine a downstream pressure at the end of a pump stroke of the pump mechanism, wait a time period, and determine a downstream pressure at the end of the time period. The programmable circuit is further programmed to assess the downstream pressure at the end of the time period, and based on the assessment, decide whether to actuate a subsequent pump stroke via the pump mechanism.

In a tenth aspect, a method of assessing downstream pressure in a medical infusion pump is disclosed. The method includes actuating a first stroke of a pump mechanism in a medical infusion pump, determining a downstream pressure at the end of the pump stroke, waiting a time period, and determining a downstream pressure at the end of the time period. The method also includes delaying a subsequent pump stroke at least until the downstream pressure is below a maximum downstream pressure by the threshold amount, and actuating a subsequent pump stroke.

In an eleventh aspect, a method of delivering a fluid from a medical infusion pump is disclosed. The method includes delivering fluid from the medical infusion pump until a downstream pressure reaches a high pressure limit. The method includes, upon reaching the high pressure limit, pausing delivery of fluid for a time period. The method further includes, upon elapsing of the time period, delivering additional fluid from the medical infusion pump.

In a twelfth aspect, a medical infusion pump is disclosed. The medical infusion pump includes a pump mechanism, a memory, and a programmable circuit arranged to control the pump mechanism and operatively connected to the memory. The programmable circuit is programmed to deliver fluid via the pump mechanism until a downstream pressure reaches a high pressure limit. The programmable circuit is also programmed to, upon reaching a high pressure limit, pause delivery of fluid for a time period. The programmable circuit is programmed to, upon elapsing of the time period, resume delivery of fluid via the pump mechanism.

In a thirteenth aspect, a method of delivering a fluid from a medical infusion pump is disclosed. The method includes initiating one or more strokes of a pump mechanism for delivering fluid from the medical infusion pump until a downstream pressure reaches a high pressure limit. The method also includes, upon reaching the high pressure limit, pausing delivery of fluid for a predetermined time. The method further includes, upon elapsing of the predetermined time, determining whether the downstream pressure remains within a predetermined threshold of the high pressure limit. The method includes upon determining that the downstream pressure is outside of the predetermined threshold, initiating one or more additional strokes of the pump mechanism for delivering additional fluid from the medical infusion pump. Through this method, the medical infusion pump delivers a maximum volume of fluid over a minimized length of time.

In a fourteenth aspect, a method of generating alarms in a medical infusion pump is disclosed. The method includes determining a severity of an alarm based on an alarm event. The method further includes selecting an alarm level from among a plurality of alarm levels based on an alarm level criteria, each alarm level corresponding to a different target group to be notified by the alarm. The method also includes activating the alarm in accordance with the selected alarm level.

In a fifteenth aspect, a medical infusion pump is disclosed. The medical infusion pump includes a pump mechanism, a memory, and a programmable circuit arranged to control the pump mechanism and operatively connected to the memory. The programmable circuit is programmed to determine a severity of an alarm based on an alarm event. The programmable circuit is also programmed to select an alarm level from among a plurality of alarm levels based on an alarm level criteria, each alarm level corresponding to a different target group to be notified by the alarm. The programmable circuit is further programmed to activate the alarm in accordance with the selected alarm level.

In a sixteenth aspect, a method of generating alarms in a medical infusion pump is disclosed. The method includes determining a severity of an alarm based on an alarm event. The method also includes selecting an alarm level from among a plurality of alarm levels based on an alarm level criteria, each alarm level corresponding to a different target group to be notified by the alarm. The method further includes activating the alarm in accordance with the selected alarm level, and maintaining activation of the alarm for a predetermined time. The method includes, if the alarm event is not addressed during the predetermined time, selecting a second alarm level from among the plurality of alarm levels. The method includes activating the alarm in accordance with the second alarm level.

BRIEF DESCRIPTION OF THE DRAWINGS

FIG. 7 illustrates an example event log displaying a history of events tracked in a medical infusion pump, according to a possible embodiment of the present disclosure;

FIG. 8 illustrates an example user association data record useable to associate users or user classes with messages or events in a medical infusion pump, according to a possible embodiment of the present disclosure;

FIG. 9 illustrates an example user data record listing and classifying users of interest to a medical infusion pump, according to a possible embodiment of the present disclosure;

DETAILED DESCRIPTION

Figure 1:
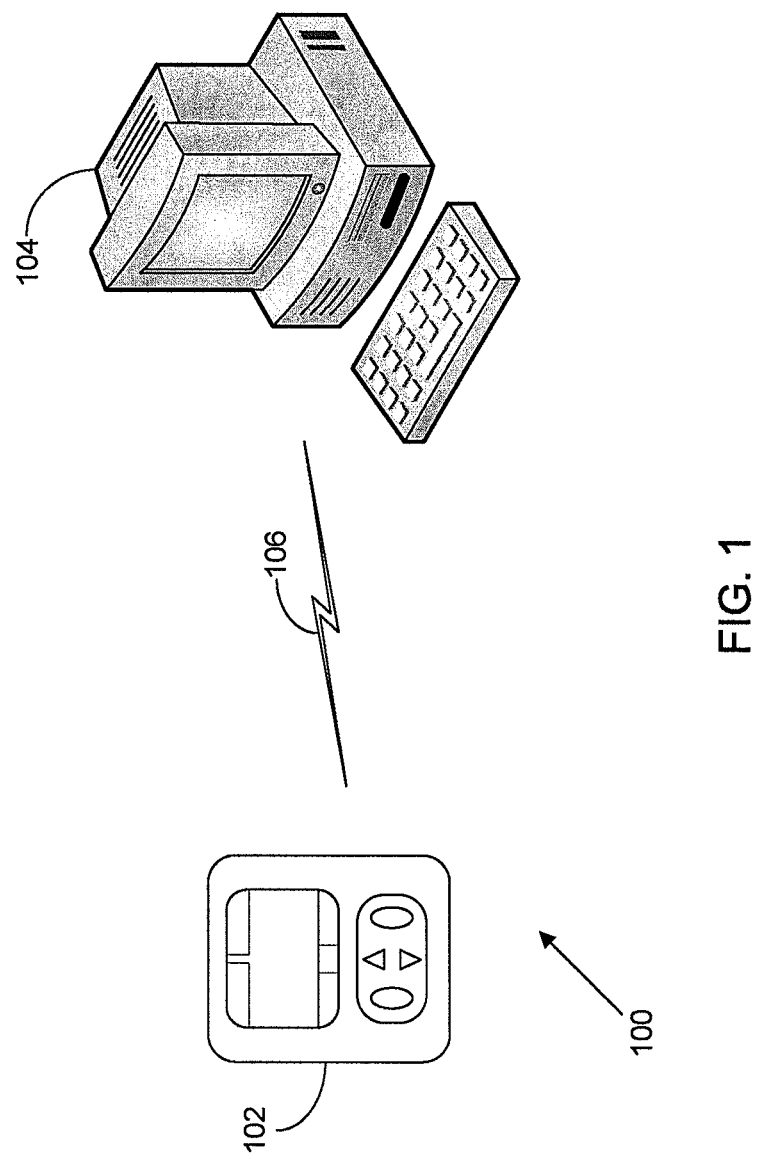
FIG. 1 illustrates a pump-computer communication system according to a possible embodiment of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates generally to fluid delivery in a medical infusion pump, and management of pumps configured to deliver fluids to a patient. The present disclosure describes features of a medical infusion pump, interactions that medical infusion pump can have with a patient (e.g. relating to fluid delivery or manual control of the pump), and interactions that the medical infusion pump can have with other users (e.g. healthcare providers or others having physical or communicative access to the pump).

The logical operations of the various embodiments of the present disclosure described herein are implemented as: (1) a sequence of computer implemented operations running on a computing system; and/or (2) interconnected machine modules within the computing system. Modules represent functions executed by program code such as commonly available programming languages or as the code found in a dynamic-link library (DLL). The implementation used is a matter of choice dependent on the performance requirements of the medical infusion pump and the computing systems with which it interfaces. Accordingly, the logical operations making up the embodiments of the present disclosure can be referred to alternatively as operations, modules, and the like.

I. Computing Environment Incorporating a Medical Infusion Pump

The following discussion is intended to provide a brief, general description of a suitable computing environment in which the invention may be implemented. Although not required, the invention will be described in the general context of computer-executable instructions being executed by a computer, for example, a hand held computer, a personal computing system, or a medical infusion pump.

FIG. 1 illustrates an exemplary embodiment of an infusion pump network 100 having a medical infusion pump 102, a computing system 104, and a communications link 106. The medical infusion pump 102 is configured to deliver therapeutic fluids, such as drugs, saline, or nutrition to a patient. Examples of medical infusion pumps 102 include ambulatory pumps, stationary pumps, and pole mounted pumps.

The computing system 104 is configured to execute computer-readable instructions, such as computer software. The computing system 104 can be located in a variety of locations such as the point of care (POC) where a patient is being treated, in a healthcare facility at a location remote from the POC, or even at an off-site location remote from the healthcare facility itself. In further embodiments, the medical infusion pump 102 acts as the computing system 104.

In the exemplary embodiment, the computing system 104 is programmed to generate and store pump protocols for execution in the context of a pump application program. Each pump protocol includes a series of pump parameters. Pump parameters refer to settings that define an operational aspect of a medical infusion pump. The pump parameters dictate the control of the pump.

By way of reference, pump protocols are collections of these pump parameters defining the variable operational characteristics of a medical infusion pump during application of a specific therapy, qualifier, and drug. The pump protocol includes a listing of operational parameters to be included in the pump, and correlates to an index for referring to a specific protocol containing a specific set of pump parameters.

Also by way of reference, a pump application program is a program having instructions (e.g., executable code, rules, and/or data) that control operation of the pump for a specific therapy or type of delivery (e.g., continuous delivery, intermittent delivery, pain control, chemotherapy, total parenteral nutrition, etc.). For example, a pump application program might contain instructions that define operation of a pump to accomplish various of the pump parameters.

The communications link 106 connects the pump 102 and computing system 104. In various embodiments, the communications link 106 can include serial or parallel connections, wired or wireless connections, and a direct or networked connection to a computer. Additionally, the pump 102 and the computing system 104 can communicate using any protocol appropriate for data communication. Examples of network connections to a computer include Intranet, Internet, and LAN (e.g., Ethernet). Examples of wired connections to a computer include USB, RS-232, Firewire, and power-line modem connection. Examples of wireless connections include bluetooth, 802.11a/b/g, infrared (IR), and radio frequency (RF).

Further details regarding use of pump parameters and protocols in the context of an infusion pump network are discussed in U.S. patent application Ser. Nos. 11/499,248, 11/499,240, 11/499,255, and 11/499,893, all filed Aug. 3, 2006, as well as U.S. patent application Ser. Nos. 11/702,922 and 11/702,925 filed Feb. 5, 2007. Each of these patent applications is hereby incorporated by reference in its entirety.

Figure 2:
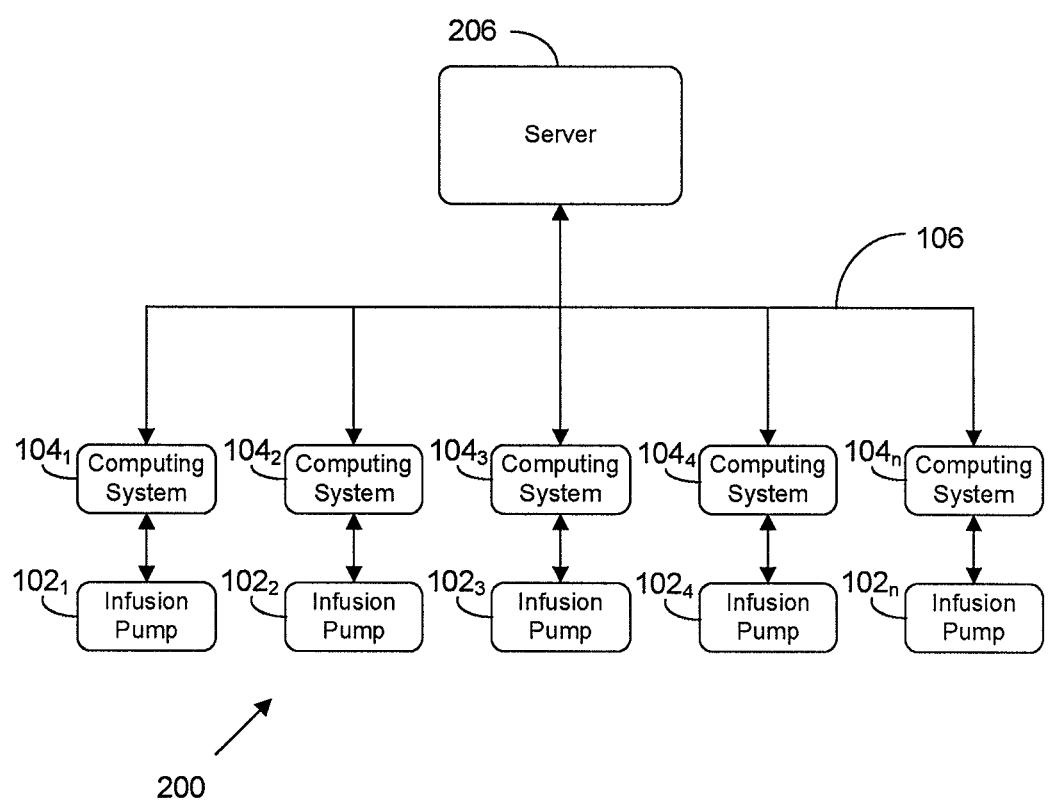
FIG. 2 illustrates an infusion pump network according to a possible embodiment of the present disclosure.

FIG. 2 illustrates an exemplary embodiment of an infusion pump network 200 having a server 206 networked with a plurality of computing systems $104_1$-$104_n$. The network 200 can be any wired or wireless network that enables data communication between the server, computing systems, and medical infusion pumps. Examples of networks include the Internet, Intranets, and LANs. Each computing system 104 can communicate with a medical infusion pump $102_1$-$102_n$ through a communication link 106.

In the exemplary embodiment, the individual computing systems $104_{1-n}$ execute software for generating and managing pump application programs and sets of pump operating parameters, and store information related to the associated medical infusion pump $102_{1-n}$. The pump application programs and sets of pump operating parameters can be stored on the server 206 and accessed by other individual computing systems $104_{1-n}$. The individual computing systems $104_{1-n}$ are also programmed to retrieve previously created pump application programs and sets of pump operating parameters that are stored on the server 206 for viewing, editing, and downloading to medical infusion pumps $102_{1-n}$. These pump application programs and pump operating parameters can be used to determine various fluid delivery algorithms, such as those described in greater detail herein.

The individual computing systems $104_{1-n}$ are also programmed to communicate various information between the medical infusion pumps $102_{1-n}$ and the server 206. In certain embodiments, the individual computing systems $104_{1-n}$ are programmed to communicate pump events to the server for storage and later processing, such as cost and operational history data tracked in the medical infusion pumps $102_{1-n}$. In further embodiments, the individual computing systems $104_{1-n}$ are programmed to communicate messages generated in the pumps to external computing systems, including the server 206 and other devices, for notification of third-party caregivers of certain occurrences (e.g. exceptions or alarms) in the pump.

In alternative embodiments, the medical infusion pumps $102_{1-n}$ can directly communicate with the server to retrieve pump application programs and sets of pump operating parameters and to provide data relating to operation of the pump. For example, the medical infusion pumps $102_{1-n}$ can be loaded with client software such as a web browser and communicate directly with the network 200, either through a wired or wireless connection as described herein.

In other alternative embodiments, one or more of the computing systems (e.g. $104_{1-n}$) is not configured to communicate directly with one of the medical infusion pumps $102_{1-n}$, but rather provides administrative access to the server 206 for generating, viewing, and editing pump application programs and sets of pump operating parameters, and for communicating data from the pump to the server. Additionally, servers, workstations, and other computing systems unaffiliated with the medical infusion pumps $102_{1-n}$ can be included in the network 200.

In yet other alternative embodiments, certain aspects of the software described herein execute in the server 206. For example, in certain embodiments the server functions as an application service provider that communicates user interface and other data entries in mark-up language such as HTML or some other language or protocol that allows a user to execute software from a remote location. In these embodiments, the server 206 can function as an application service provider in which the server provides access to the software for generating and storing pump application programs and pump protocols that a user can create and download to a medical infusion pump, as well as for managing user databases, pump histories, message and alarm distribution, and other events. For example, the server 206 could be located at a pump manufacture, pharmaceutical manufacture, pharmacist, or some other third party separate from the user. The server 206 in such an embodiment can be accessed either from an individual computing system 104 or by a medical infusion pump 102 that has networking capabilities and client software.

Example embodiments of a server 206 and a medical infusion pump 102 having a web browser are disclosed in U.S. patent application Ser. No. 11/066,425, which was filed on Feb. 22, 2005 and is entitled Server for Medical Device, the entire disclosure of which is hereby incorporated by reference.

Figure 3:
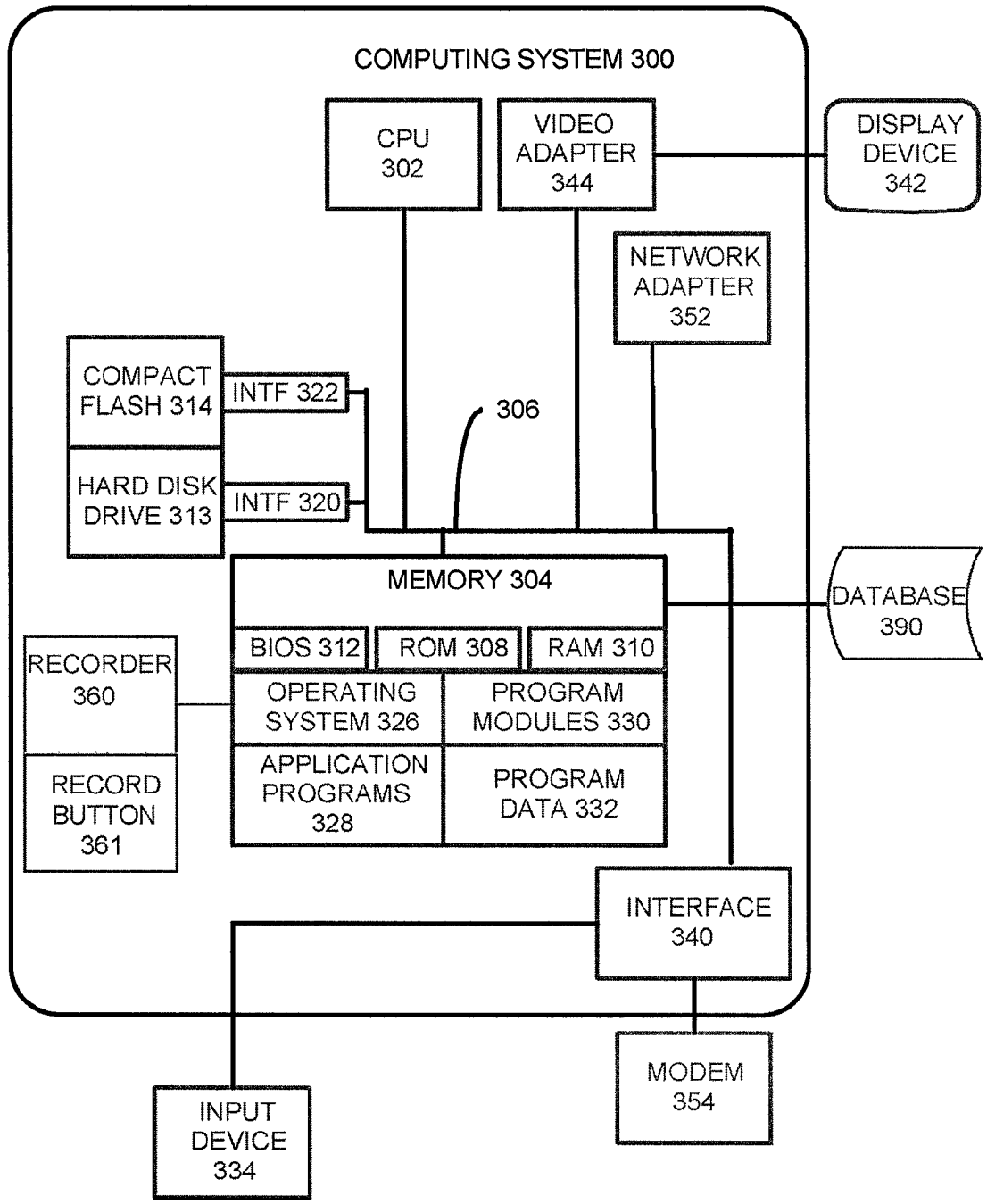
FIG. 3 illustrates the architecture of a computing system that can be used to implement aspects of the present disclosure.

FIG. 3 illustrates an exemplary architecture that can be used to implement aspects of the present disclosure, including the computing systems 104 or the server 206. The computing system architecture includes a general purpose computing device in the form of a computing system 300. The computing system 300 can be used, for example, as the computing system or server of FIG. 2, and can execute program modules included in the administrative software or user software disclosed below.

The computing system 300 including at least one processing system 302. A variety of processing units are available from a variety of manufacturers, for example, Intel or Advanced Micro Devices. The computing system 300 also includes a system memory 304, and a system bus 306 that couples various system components including the system memory 304 to the processing unit 302. The system bus 306 may be any of a number of types of bus structures including a memory bus, or memory controller; a peripheral bus; and a local bus using any of a variety of bus architectures.

The system memory 304 can include read only memory (ROM) 308 and random access memory (RAM) 310. A basic input/output system 312 (BIOS), containing the basic routines that help transfer information between elements within the computing system 300, such as during start up, is typically stored in the ROM 308.

The computing system 300 can also include a secondary storage device 313, such as a hard disk drive, for reading from and writing to a hard disk (not shown), and/or a compact flash card 314.

The hard disk drive 313 and compact flash card 314 are connected to the system bus 306 by a hard disk drive interface 320 and a compact flash card interface 322, respectively. The drives and cards and their associated computer readable media provide nonvolatile storage of computer readable instructions, data structures, program modules and other data for the computing system 300.

Although the exemplary environment described herein employs a hard disk drive 313 and a compact flash card 314, other types of computer-readable media, capable of storing data, can be used in the exemplary system. Examples of these other types of computer-readable mediums include magnetic cassettes, flash memory cards, digital video disks, Bernoulli cartridges, CD ROMS, DVD ROMS, random access memories (RAMs), or read only memories (ROMs).

A number of program modules may be stored on the hard disk 313, compact flash card 314, ROM 308, or RAM 310, including an operating system 326, one or more application programs 328, other program modules 330, and program data 332. A user may enter commands and information into the computing system 300 through an input device 334. Examples of input devices might include a keyboard, mouse, microphone, joystick, game pad, satellite dish, scanner, digital camera, touch screen, and a telephone. These and other input devices are often connected to the processing unit 302 through an interface 340 that is coupled to the system bus 306. These input devices also might be connected by any number of interfaces, such as a parallel port, serial port, game port, or a universal serial bus (USB). Wireless communication between input devices and interfaces 340 is possible as well, and can include infrared, bluetooth, 802.11a/b/g, cellular, or other radio frequency communication systems. A display device 342, such as a monitor or touch screen LCD panel, is also connected to the system bus 306 via an interface, such as a video adapter 344. The display device 342 might be internal or external. In addition to the display device 342, computing systems, in general, typically include other peripheral devices (not shown), such as speakers, printers, and palm devices.

When used in a LAN networking environment, the computing system 300 is connected to the local network through a network interface or adapter 352. When used in a WAN networking environment, such as the Internet, the computing system 300 typically includes a modem 354 or other communications type, such as a direct connection, for establishing communications over the wide area network. The modem 354, which can be internal or external, is connected to the system bus 306 via the interface 340. In a networked environment, program modules depicted relative to the computing system 300, or portions thereof, may be stored in a remote memory storage device. It will be appreciated that the network connections shown are exemplary and other methods of establishing a communications link between the computing systems may be used.

The computing system 300 might also include a recorder 360 connected to the memory 304. The recorder 360 includes a microphone for receiving sound input and is in communication with the memory 304 for buffering and storing the sound input. The recorder 360 also can include a record button 361 for activating the microphone and communicating the sound input to the memory 304. The computing system can also include a database 390 for storage of data. The database 390 can be accessible via the memory 304 (either integrated therein or external to) and can be formed as any of a number of types of databases, such as a hierarchical or relational database.

A computing device, such as computing system 300, typically includes at least some form of computer-readable media. Computer readable media can be any available media that can be accessed by the computing system 300. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the computing system 300.

Communication media typically embodies computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 4:
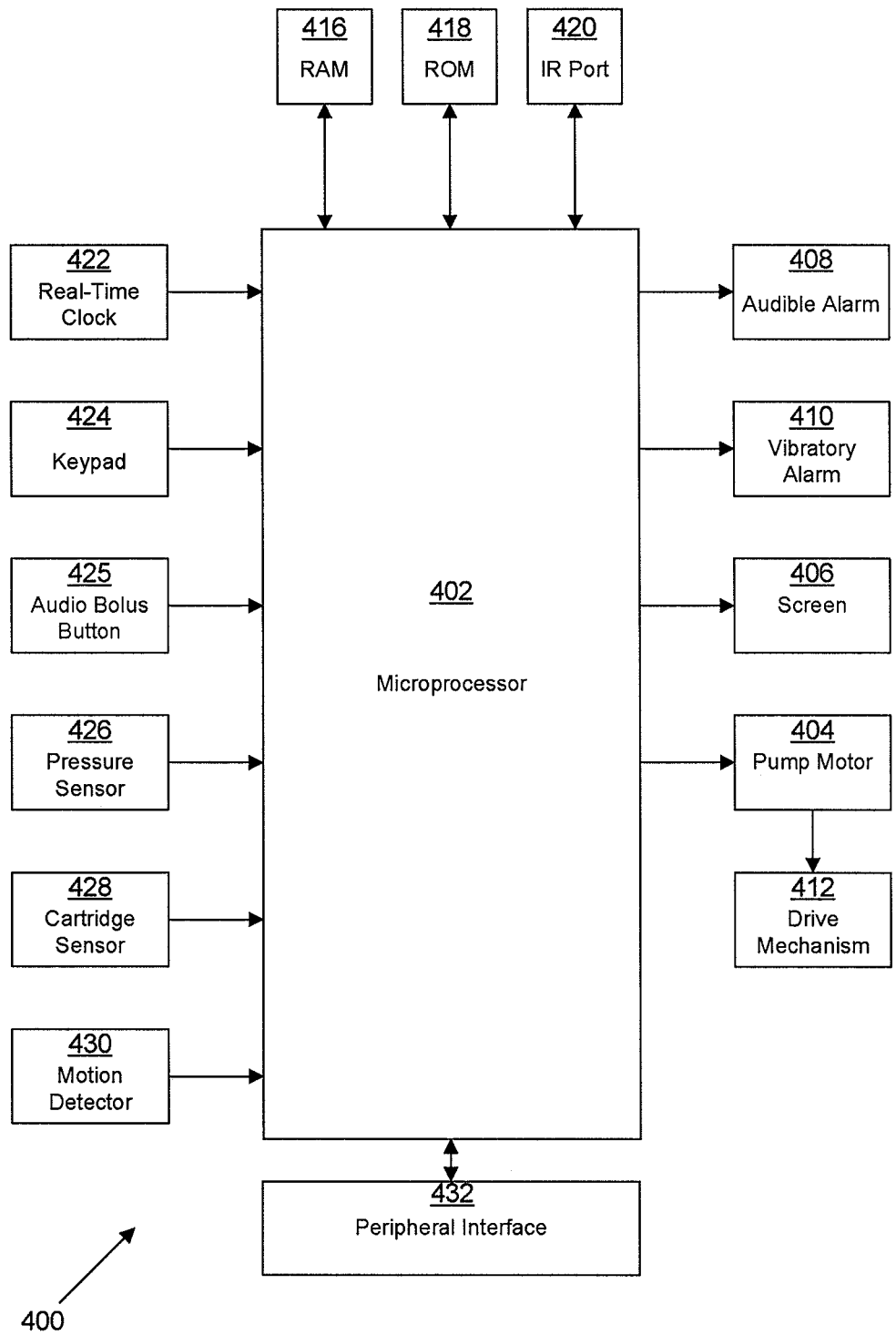
FIG. 4 illustrates the architecture of a pump that can be used to implement aspects of the present disclosure.

FIG. 4 illustrates the architecture of a medical infusion pump 400 that can be used to implement aspects of the present disclosure. In general, the medical infusion pump 400 is a programmable pump configured to deliver fluids (e.g. fluidic drugs) to patient, such as through use of an infusion set. The medical infusion pump 400 executes one or more application programs, as described above in conjunction with FIG. 1, to accomplish fluid delivery to a patient.

In the medical infusion pump 400, a microprocessor 402 is in electrical communication with and controls a pump motor 404, a screen 406, an audible alarm 408, and a vibratory alarm 410. Other embodiments can use a microcomputer, or any other type of programmable circuit, in place of the microprocessor.

The pump motor 404 drives a drive mechanism 412. The drive mechanism 412 delivers the therapeutic fluid to a patient. The drive mechanism can be connected to a plunger system, a peristaltic drive mechanism, or another type of fluid delivery system.

The screen 406 can have many different configurations such as an LCD screen. The screen 406 displays a user interface that presents various items of information useful to a patient or caregiver. An alarm provides actual alarms, warnings, and reminders in the pump. The audible alarm 408 can be a beeper or otherwise provide audible notifications including actual alarms, warnings, and reminders. Similar to other portable electronic devices such as a cellular telephone, the vibratory alarm 410 provides an alarm to either supplement the audio alarms or replace the audio alarm when an audible beep would be disruptive or not heard. A user can selectively enable or disable the audible 408 and vibratory 410 alarms. In one possible embodiment, however, both the audible 408 and vibratory 410 alarms cannot be disabled at the same time.

The microprocessor 402 is in electrical communication with a random access memory (RAM) 416 and a read only memory (ROM) 418, which are onboard the pump 400 but external to the microprocessor 402 itself. In one possible embodiment, the microprocessor 402 includes internal memory as well. The RAM 416 is a static RAM stores that data that can change over time such as pump settings and a historical log of events experienced by the medical infusion pump 400. The ROM 418 stores code for the operating system and the application programs. The ROM 418 can be any type of programmable ROM such as an EPROM.

An infrared (IR) port 420 is in electrical communication with the microprocessor. As explained in more detail below, the IR port 420 provides data communication with an external device such as a computer for programming an application program, programming pump settings, and downloading historical data logs. The medical infusion pump 400 can include other types of communication ports in place of or in addition to the IR port 420. Examples of other possible communication ports include a radio frequency (RF) port or a port that provides a hard-wired data communication link such as an RS-232 port, a USB port, or the like.

Optionally, an additional nonvolatile memory can be incorporated into the pump and interfaced with the microprocessor 402, such as a flash memory. This additional nonvolatile memory can be configured to store data collected by the pump, such as a history of events in the medical infusion pump, alarm and message information, user records for healthcare personnel authorized to operate the pump, and other information.

A real-time clock 422 provides a clock signal to the microprocessor 402. An advantage of having a real-time clock 422 is that it provides the program with the actual time in real-time so that the programs executed by the medical infusion pump can track and control the actual time of day that drug delivery and other events occur. Various durations described here are used for alerts, alarms, reminders, and other functions. In one possible embodiment, the timers are formed by the real-time clock 422 and software executed by the microprocessor 402.

A keypad 424 also provides input to the microprocessor 402. Although other possible types of keypads are possible, one type of keypad has four buttons and is a membrane-type of keypad, which provides resistance to water and other environmental conditions. The keypad 424 contains soft keys for which the function of the keys can change as a user executes different menu selections and commands.

An audio bolus button 425 optionally provides input to the microprocessor 402. The audio bolus button 425 can program the pump 400 to audibly administer a bolus of drugs or other therapeutic fluids without requiring visual confirmation using the pump. In an example embodiment, the audio bolus button 425 can be pressed a series of times to trigger bolus delivery of a selected volume, based on a preprogrammed trigger granularity. A single button press can represent a bolus of 5 grams, as selected by a user, and subsequent presses of the audio bolus button can represent multiples thereof.

Other inputs into the microprocessor 402 can include an occlusion sensor 426, which is sensitive to occlusions in the therapeutic fluid delivery line; a cartridge sensor 428, which is sensitive to the presence of a therapeutic fluid cartridge; and a motion detector 430, which detects motion of a gear (not shown) in the drive mechanism 412. In an exemplary embodiment, the cartridge sensor 428 includes one or more sensors configured to detect insertion of a therapeutic fluid cartridge. The pump 400 can detect the type of cartridge present via a mechanical interface, and can include in the pump software instructions regarding operation in conjunction with the cartridge. Examples of cassette sensing features are described, for example, in U.S. Pat. No. 5,531,697, filed on Apr. 15, 1994, issued on Jul. 2, 1996, and entitled Systems and Methods for Cassette Identification for Drug Pumps.

A peripheral interface 432 allows additional systems to be added to the pump 400, such as various communication and functional systems. Example systems that can be interfaced with the pump include a bar code reader or a communication module, or other devices such as those devices described below in conjunction with FIG. 5

Figure 5:
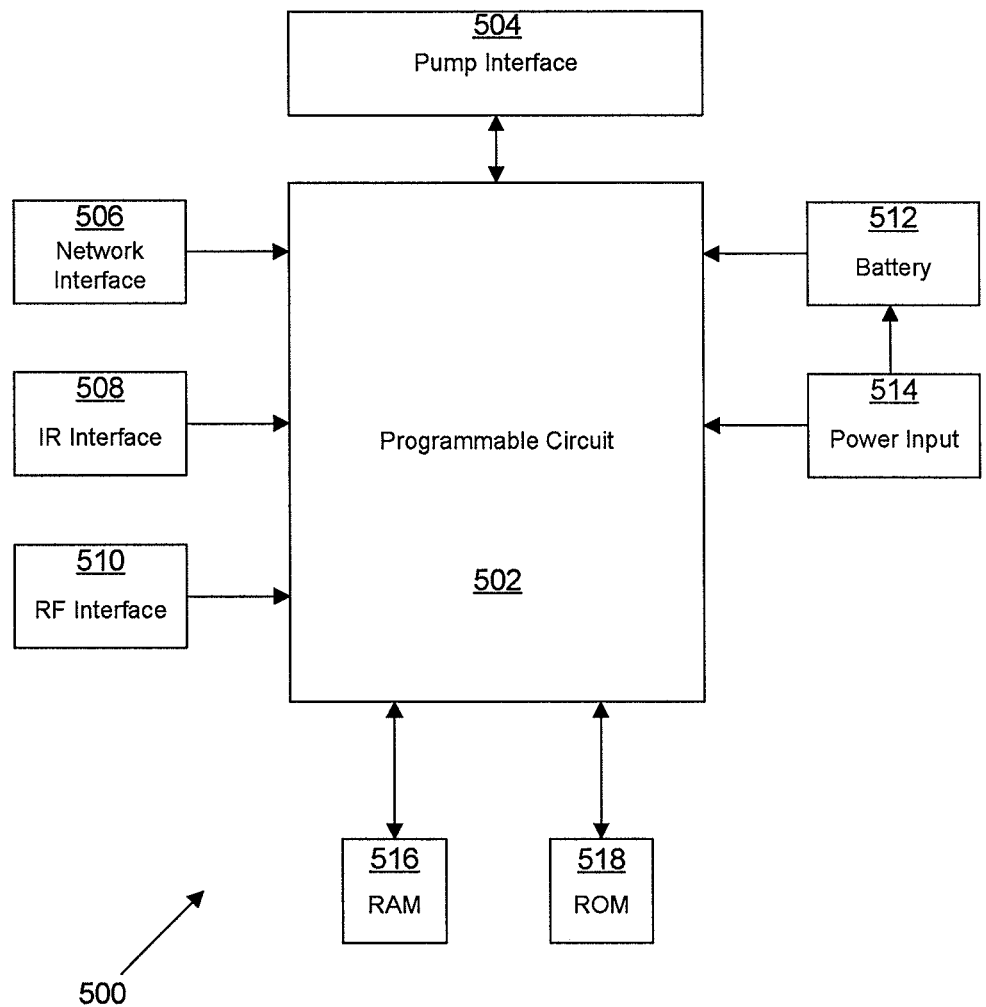
FIG. 5 illustrates the architecture of a pump peripheral device that can be used to implement aspects of the present disclosure.

FIG. 5 illustrates a peripheral device 500 that can interface with the medical infusion pump described in FIG. 4. The peripheral device 500 generally provides extended functionality to the medical infusion pump 400. In the embodiment shown, the peripheral device 500 provides extended communication and computation functionality to the medical infusion pump, thereby offloading a number of tasks from that system and freeing resources used for delivering fluids to the patient.

The peripheral device 500 includes a programmable circuit 502, which is configured to execute program instructions as directed by the microprocessor 402 of the medical infusion pump 400 and also as received from external computing systems. The programmable circuit 502 also optionally includes various additional operational logic configured to access memory, and to respond to the various interfaces to the programmable circuit. In one embodiment, the programmable circuit 502 includes a microcontroller. The microcontroller can be programmable in any of a number of programming languages, such as assembly language, C, or other low-level language. In alternate embodiments, the programmable circuit 502 includes a programmable logic device (PLD) such as a field programmable gate array (FPGA), Complex Programmable Logic Device (CPLD), or Power ASIC (Application Specific Integrated Circuit). In these embodiments, a hardware description language such as Verilog, ABEL, or VHDL defines operation of the programmable circuit.

The peripheral device 500 also includes an electrical interface 504 communicatively interfaced with the programmable circuit. The electrical interface 504 provides an electrical and data connection between the programmable circuit 502 and connecting circuitry of a medical infusion pump (e.g. the peripheral interface 432 of the medical infusion pump of FIG. 4). In the embodiment shown, the electrical interface 502 can be a serial or parallel interface, such as a USB interface, which allows the peripheral device to both (1) transmit and receive data along the interface, and (2) receive/transmit electrical power, such as to power either the medical infusion pump 400 or peripheral device 500.

A variety of additional interfaces also connect to the programmable circuit 502, including a network interface 506, an infrared interface 508, and a wireless interface 510. Each of these interfaces provides data communications connections with corresponding computing systems external to the medical infusion pump. The network interface 506 provides a wired connection to a packet-based, IP-addressable network, such as the Internet or a Local Area Network. The infrared interface 508 provides a direct device-to-device connection allowing data communication with nearby handheld or portable devices, and allowing the peripheral device 500 to receive data from such devices. The wireless interface 510 also provides a data connection to external computing systems, and can use any of a number of wireless communication protocols or networks, such as 802.11a/b/g/n, mesh networking, or some proprietary RF communication protocol. Other interfaces can be integrated into the peripheral device 500 or the medical infusion pump 400 as well, depending upon the particular implementation and desired communication systems used with the medical infusion pump.

The peripheral device 500 also includes a battery 512 and power input 514 interfaced to the programmable circuit 502. The battery 512 provides a power source to the circuitry in the peripheral device 500, and can also provide power to the medical infusion pump 400 via the pump interface 504. In certain embodiments, the battery is a rechargeable Lithium-ion battery pack that is rechargeable via the power input 514. The power input 514 receives power from an external source (e.g. an external AC plug), and converts that for use in the peripheral device (as distributed by the programmable circuit 502) and for recharging the battery 512.

The peripheral device also includes various types of memory communicatively interfaced to the programmable circuit, including a RAM 516 and a ROM 518. The RAM 516 and ROM 518 are used to execute program instructions provided to the peripheral device, such as for managing data input/output for the medical infusion pump. Additional memory types, such as a flash memory, can be used as well.

In certain embodiments, the peripheral device 500 can be incorporated into the medical infusion pump 400 of FIG. 4. In such embodiments, the programmable circuit 502 can be eliminated, with the various units interfaced thereto directly connecting to the microprocessor 402 of that system. In other embodiments, the peripheral device is separate from the medical infusion pump, requiring interface circuitry 504 and 432 for forming a connection therebetween.

Additional functionality can be included in the peripheral device 500 as well, based on the specific functionality desired for use with the medical infusion pump. Example additional functionality can include input/output devices, such as a bar code reader, fingerprint scanner, or other biometric reader.

Figure 6:
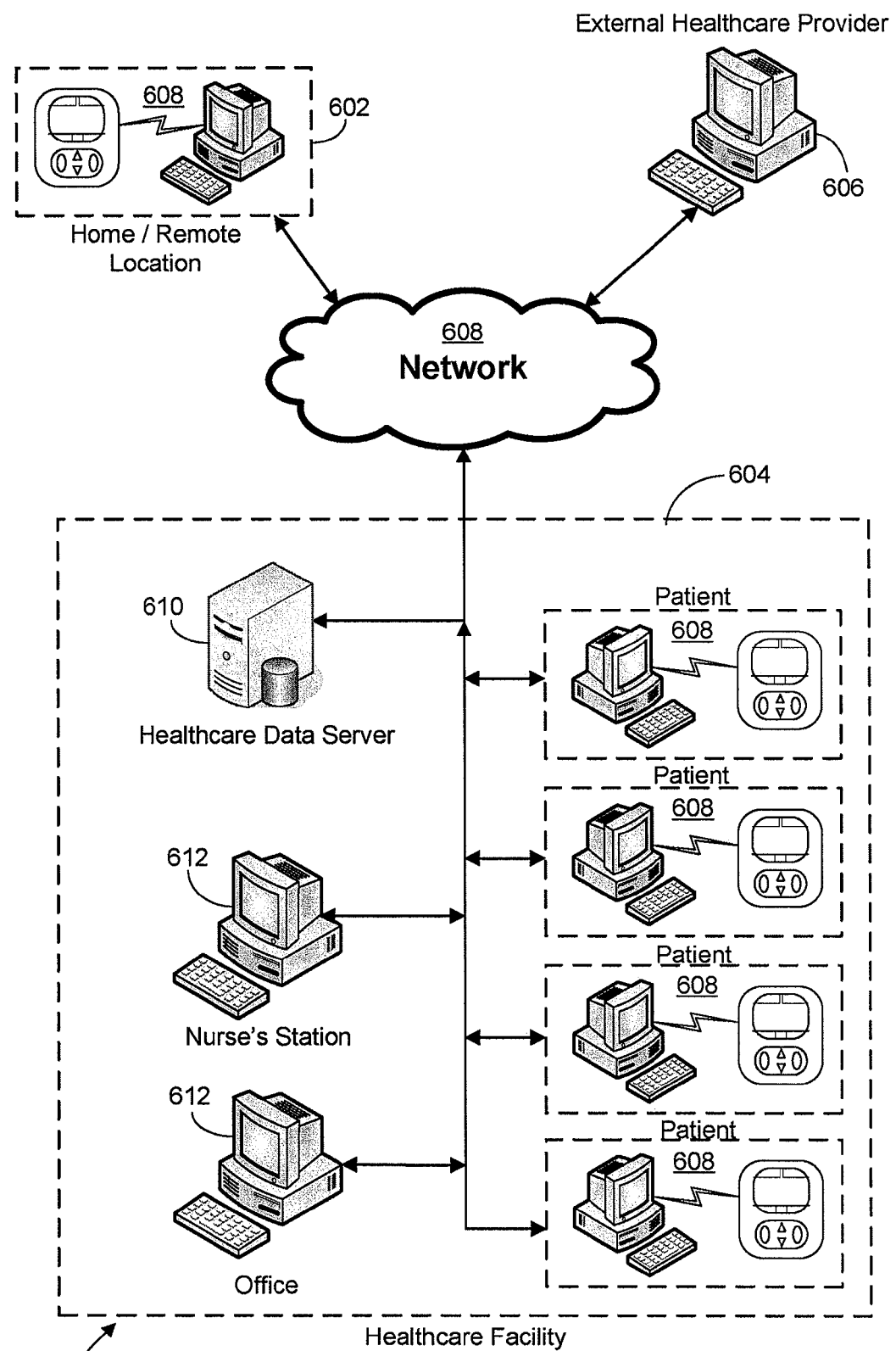
FIG. 6 illustrates a possible layout of a medical care network incorporating medical infusion pumps, according to a possible embodiment of the present disclosure.

Referring now to FIG. 6, a possible layout of a medical care network 600 is shown in which medical infusion pumps are used, according to a possible embodiment of the present disclosure. The medical care network 600 relates patients and healthcare professionals to each other using a variety of computing systems and medical devices, such as servers, medical infusion pumps, and other computing systems. As such, the medical care network illustrates one of many possible implementations of network 100 of FIG. 1.

In the embodiment shown, the medical care network includes one or more medical infusion pumps, one or more computing systems that can be communicatively connected to those medical infusion pumps, one or more servers managing data relating to the medical infusion pumps, and other computing systems used by patients or healthcare professionals (e.g. nurses, doctors, pharmacists, or other clinicians). Details regarding the specific network 600 shown are described below; however, the network 600 is intended as exemplary, and various additional systems and devices can be included which are not currently shown.

In the embodiment shown, the medical care network 600 includes and interconnects a number of different physical entities/locations, including a home or remote location 602, a healthcare facility 604, and an external healthcare provider 606. The home or remote location 602 corresponds to a location outside of a healthcare facility at which a user may want to use a medical infusion pump, and may need to communicate data with a healthcare professional or with a server, such as for monitoring the status of the medical infusion pump. Each location can include, for example, an infusion pump network 608, such as the network described above in conjunction with FIG. 1.

The healthcare facility 604 corresponds generally to a hospital or clinic at which a number of patients may reside, as well as entities related to the facility (e.g. affiliated clinics or other institutions). In the embodiment shown, the healthcare facility 604 is arranged to accommodate a number of patients, by providing those patients with a medical infusion pump and a computing system for data communications with the pump. In the embodiment shown, the various patients can each be associated with an infusion pump network 608 such as shown in FIG. 1. The infusion pump networks 608 within the healthcare facility 604 can correspond to networks present in patient rooms, or computing networks surrounding a patient at the facility. Other possibilities for the configuration of the infusion pump networks 608 can exist as well.

The healthcare facility 604 further includes a healthcare data server 610 and a plurality of computing systems 612 not directly associated with the medical infusion pumps or infusion pump networks 608. The healthcare data server 610 and computing systems 612 are typically used by healthcare professionals for patient monitoring and care management, billing, and other purposes.

Each of the computing systems at the healthcare facility 604, including those interfaced with medical infusion pumps, are communicatively interconnected, allowing communication among the various infusion pump networks 608 and with the healthcare data server 610 and computing systems 612. The systems can be communicatively connected by any of a variety of communicative connections, including various wired and wireless Local Area Network connections.

The external healthcare provider 606 can correspond to various remote healthcare providers or healthcare-related entities, such as remote physicians, remote specialists, health insurance companies, or other entities. The external healthcare provider 606 generally receives a certain subset of the data related to one or more patients within the network 600, such as test information, billing information, diagnosis information, or other information.

Each of the entities within the network 600 are communicatively interconnected by a network 614, which represents a communication network in which data can be transferred, such as the Internet or some other Wide Area Network (LAN or WAN). The network 614 interconnects the various locations and computing systems at those locations, allowing data communication among the various locations. Through use of the network 614, remote locations can store or access information from other locations and/or systems. For example, the external healthcare provider 606 can access information stored on the healthcare data server 610 at the healthcare facility 604. Or, data can be uploaded to the healthcare facility from one of the local (at the facility) infusion pump networks 608, or remote infusion pump networks 608 at one of the remote locations 602. Other examples of data sharing and data communications are possible as well.

Referring now to FIGS. 7-9, various data records are displayed which track certain pump actions, such as programming, messages, alarms, and other information. The data records displayed can be stored in any of a number of computing systems described herein, such as the medical infusion pumps, computing systems, or healthcare data servers described in FIG. 6. Although a certain set of data records are shown, these records are intended as exemplary only. Rather, these records can be combined with each other or with other records, and can be made accessible to various other systems for processing of medical infusion pump data and management of medical infusion pumps.

In one embodiment, each of the event logs and data records described herein contain data relating to a single medical infusion pump, and are stored in a local memory of that pump or within a computing systems in an infusion pump network associated with that pump (as in FIG. 1). In a further embodiment, the event logs and/or data records are stored in a remotely accessible server or other computer systems, such as the healthcare information server of FIG. 6. In such further embodiments, the event logs and data records of many pumps optionally are combined into a single event log or data record.

FIG. 7 illustrates an example event log 700 displaying a history of events tracked in a medical infusion pump, according to a possible embodiment of the present disclosure. The event log 700 displays generally a history of various changes in status of the medical infusion pump which may occur during operation of a medical infusion pump. The event log 700 can include, for example: an identification of the pump in which the event occurs; a name of a patient with whom the pump is associated; a type of event; a date and time of the event; and a description of the event. Additional information can be stored in the event log 700 as well, such as alarm states related to the event or other information relating to the patient, the pump, pump activity, or pump programs in use within the pump.

FIG. 8 illustrates an example user association data record 800 useable to associate users or user classes with messages or events in a medical infusion pump, according to a possible embodiment of the present disclosure. The user association data record 800 generally associates specific healthcare personnel with various types of alarms or messages that can occur in a medical infusion pump.

In the embodiment shown, the user association data record 800 lists a message type, target individuals, communication type, and severity. The message type corresponds to a general classification for the message which indicates a class of actions occurring in the medical infusion pump. As shown, message types include drug alarms, notification messages, pump exceptions, and patient alerts. Other types of messages are possible as well. The target individuals correspond to the specific individuals or classes of individuals who are intended to receive the specific message indicated by the message type and communication type, such as doctors, nurses, pharmacists, clinicians, or other classes of individuals or named individuals. The communication type corresponds to the communication of the specific type of event occurring in the medical infusion pump. Example communication types indicate when the pump is approaching the end of a drug supply or has reached the end of the drug supply; errors during operation of the medical infusion pump; drug delivery limits reached or exceeded (soft limits or hard limits) and/or the amount of time at which the delivery limits are exceeded; patient modification of pump programs; and patient assistance requests. Other communication types are possible as well.

As shown, each communication type is associated with a severity level, which generally corresponds to the required promptness with which a response to the message is required. For example, a pump exception in which the pump ceases operation will require a quicker response from a caregiver or pump technician as compared to an informational message, which may not require any intervention at all. In the embodiment shown, three severity levels are illustrated: low, medium and high. A low severity level generally can be assigned to messages/communications that do not require immediate action, but may require action if that event persists. A medium severity level may correspond to a message or alarm indicating that action should be taken by a healthcare provider, but that the action may not need to be taken immediately. A high severity level corresponds to an indication that the pump has ceased normal expected operation and will require intervention from a healthcare provider. Other arrangements of messages, alarms, and security levels are possible as well.

The user association data record 800 associates individuals, or classes of individuals, with each message or alarm. Each class of individuals represents a predefined set of individuals having similar access and usage rights to a medical infusion pump. Example classes could include doctors, nurses, pharmacists, patients, or clinicians. Other classes may be included as well, based on the specific use of the pump. For example, a local usage class can associate certain messages and alarms with individuals that can login directly onto a medical infusion pump using the software stored on that pump. A remote usage class can associate other messages or alarms with individuals that typically do not use the pump in person, but monitor its activity. In certain embodiments, individuals also singly represent a class (with that class including only that individual as a member).

In certain embodiments, the user association data record 800 is customizable by a healthcare professional or other user. For example, in one embodiment, the user association data record 800 is stored on a healthcare information server, such as the one shown in FIG. 6. In such an embodiment, a user at any of a variety of computing systems communicatively connected to the server can use a web-based user interface to create or modify the user association data record. In another embodiment, the user association data record 800 is stored on a medical infusion pump, and healthcare providers or other users can edit the record using the medical infusion pump, a computing system in an infusion pump network (e.g. network 100 of FIG. 1), or a computing system within a medical care network such as network 600 of FIG. 6.

FIG. 9 illustrates an example user data record 900 listing and classifying users of interest to a medical infusion pump, according to a possible embodiment of the present disclosure. The user data record defines classes of users that are provided access privileges, assigned messages, or assigned alarms from one or more medical infusion pumps. The user data record 900 can be used in conjunction with the user association data record (e.g. the user association data record 800 of FIG. 8) to link specific users' contact information with messages or alarms to ensure that the user is notified of events occurring in one or more medical infusion pumps.

The user data record 900 includes a unique user identification number, the name of the user, one or more classes to which the user belongs, and one or more contact methods for communicating with the user. In further embodiments, additional information is included in the user data record as well, such as the name of a healthcare facility with which the user is affiliated, or details regarding the user's identity (e.g. a doctor's specialty, a nurse's typical shift, etc.).

The user data record 900 can be accessed following an event in a medical infusion pump, such as a message or alarm, to determine which individuals should be notified of the event and how to contact those individuals. In one possible embodiment where the record 900 is used in conjunction with a user association data record 800 as shown in FIG. 8 to send an alarm or message to users, the user association data record 800 is first accessed to determine one or more classes of users or individual users that should be notified. The user data record 900 is then parsed to access information regarding how to contact those users or classes of users.

The contact information included in the user data record 900 includes one or more methods of communicating messages to a user, such as via email, cellular communications, pager, or text messages.

Additional details regarding the data records of FIGS. 7-9, and their use in the networks and systems of FIGS. 1-6, are described below.

B. Programmable Features Incorporated into a Medical Infusion Pump Network

FIGS. 1-9, above, describe certain aspects of medical infusion pumps and communication networks including medical infusion pumps, including various types of computing systems and communicative connections used in management and operation of the pumps. Now referring to FIGS. 10-23, applications of specific features incorporated into a medical infusion pump or a network including a medical infusion pump are described.

The applications and features described herein can be implemented as software, programmable hardware, and user interfaces integrated into the medical infusion pump, or a computing system interfaced with one or more medical infusion pumps. For example, one or more features are implemented in a pump application program able to be loaded onto and execute on a medical infusion pump. These programmable features relate generally to handling and routing of alarms and messages within a medical infusion pump network, tracking costs incurred by use of a medical infusion pump, and improved performance of medical infusion pumps with respect to delivery of fluids to patients.

1. Localized Alarm and Message Handling

Figure 10:
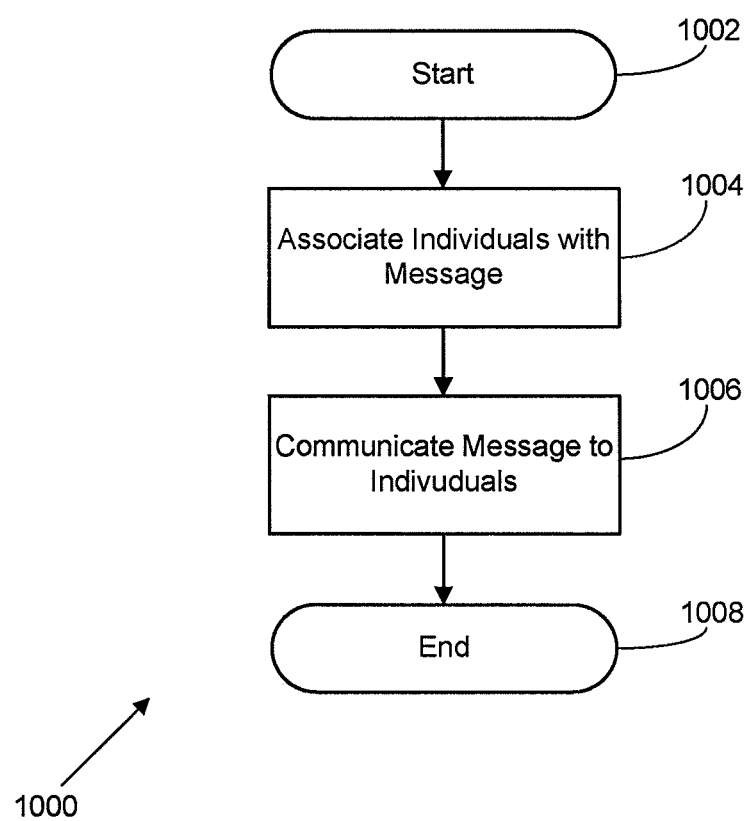
FIG. 10 illustrates a flowchart of methods and systems for localized alarm and message handling in a medical infusion pump, according to a possible embodiment of the present disclosure.
Figure 11:
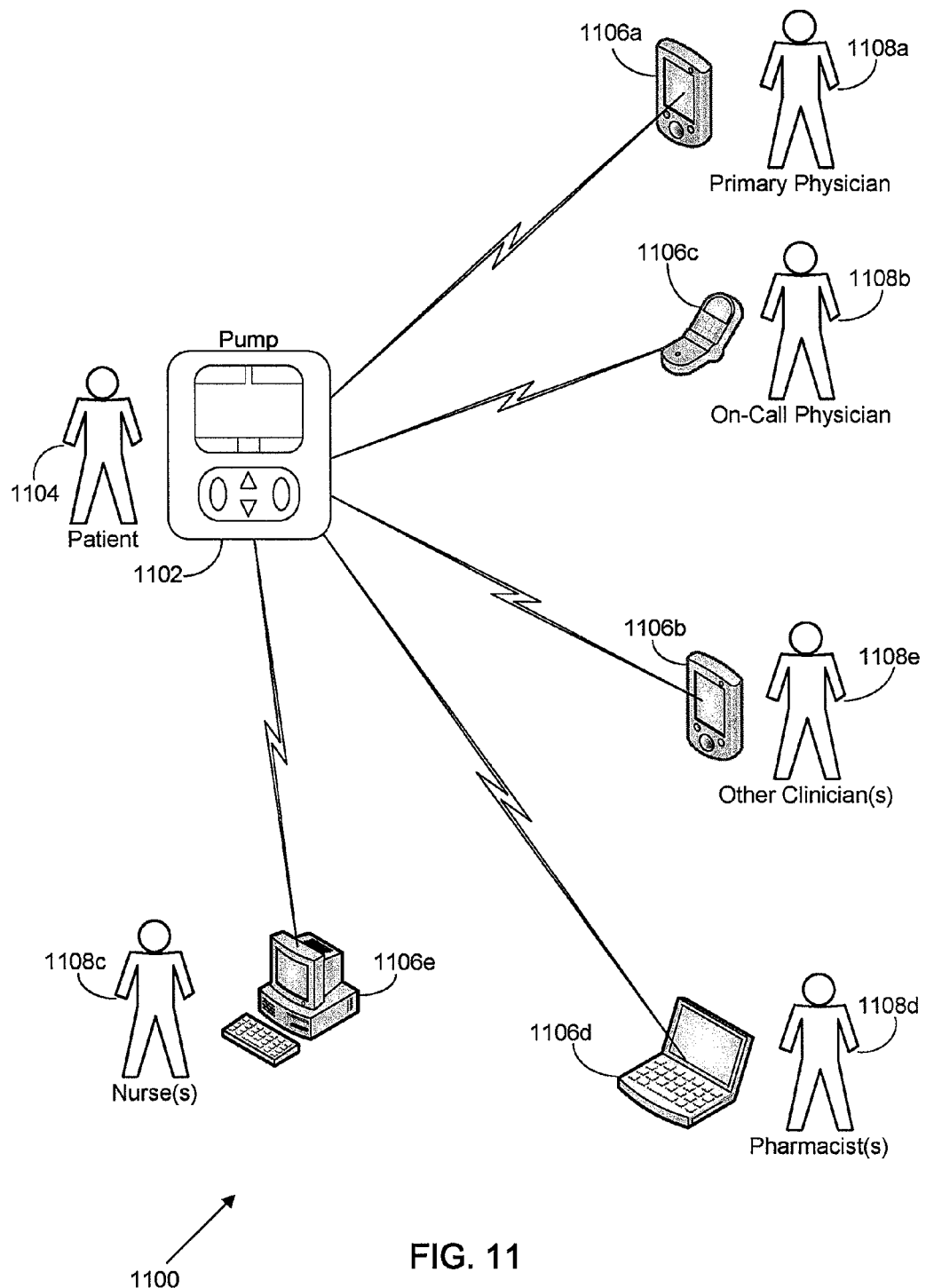
FIG. 11 illustrates a pump-user communication system useable for targeted alarm and message handling in a medical infusion pump, according to a possible embodiment of the present disclosure.

FIGS. 10-11 describe a possible implementation for managing and localizing messages and alarms generated in one or more medical infusion pumps. Messages correspond to data generated in a medical infusion pump and intended to be communicated to a user, such as the patient or a healthcare provider monitoring the activity of the pump. Messages can relate to any of a variety of conditions in a medical infusion pump, such as current operating conditions of the pump; current programs executing in the pump; changes to pump operation or changes to a pump environment (i.e. relating to patient feedback, drug supply, light, temperature, or other sensed conditions); or other informational messages communicating the status of the pump to a user. Alarms generally correspond to alerting conditions for notifying a user (e.g. the patient or a healthcare provider) to assess the need for intervention in the pump's activity. The systems and methods are generally implemented in a medical care network, such as the example medical care network described in conjunction with FIG. 6, above.

FIG. 10 illustrates a flowchart of a process 1000 for localized alarm and message handling in a medical infusion pump, according to a possible embodiment of the present disclosure. The process 1000 generally provides targeted alarms and messages to a user or a group of users to whom the message is relevant, based on association of that user with the message and the medical infusion pump in which the message is generated. The process is instantiated at a start operation 1002, which corresponds to initial operation of a medical infusion pump.

An association module 1004 associates one or more individuals with one or more messages. The individuals associated with the message generally correspond to individuals caring for a patient (e.g. healthcare providers), patients, or others requiring notification of certain message or alarm events. The messages correspond to notifications generated by the medical infusion pump relating to its operational status. The messages can include alarms or other informational notifications.

Generally, the association module 1004 assigns certain individuals or classes of individuals to each of the messages potentially generated by a medical infusion pump. In certain embodiments, the association module 1004 links records relating to individuals with records relating to messages and alarms, such as by linking the records in a database, spreadsheet, or flat file format.

In one embodiment, the association module 1004 generates user records and user association records, such as are described above in conjunction with FIGS. 7-9. In accordance with these embodiments, the association module 1004 can operate on the medical infusion pump generating the message or alarm, storing the various records in a memory of the pump. Alternately, the association module 1004 can operate on and store records within a computing system communicatively connected to the pump, such as a computing system in an infusion pump network or a healthcare data server.

Classes of individuals associated with messages can include a predefined class of individuals, such as doctors, nurses, clinicians, pharmacists, or patients. Classes of individuals can also include modifiable groups of one or more individuals, such as a user-defined listing of individuals defined in database records. For example, separate classes of individuals can be created for varying working shifts at a hospital or other healthcare facility, with the system configured to associate messages with the currently-working group of individuals (e.g. nurses, doctors, or other clinicians). These modifiable classes can be altered using the association module 1004, executing on the medical infusion pump or a computing system communicatively connected to the medical infusion pump.

A communication module 1006 communicates a message to one or more individuals or classes of individuals, based on records generated by the association module 1004. The communication module 1006 communicates the message from the medical infusion pump at which it is generated to the individuals associated with the message. In embodiments where the association module 1004 and related association records are stored on the medical infusion pump or within an infusion pump network that is local to the pump (i.e. in near proximity), the communication module 1006 communicates the message from the pump to the appropriate individuals (through one or more computing systems, as necessary). In embodiments where the association module 1004 and related association records are stored and executed on a healthcare data server or other computing system remote from the medical infusion pump, the medical infusion pump sends the generated message to that computing system, which in turn accesses the user association records and user records to determine which users to communicate the message to. The remote computing system (e.g. healthcare data server or other system) then communicates the message to the user(s).

In certain embodiments, the communication module 1006 triggers communication of the message to users upon generation of the message in the medical infusion pump. In other embodiments, the communication module 1006 stores the message on the medical infusion pump or a server (depending upon the location of the user records and user association records generated by the association module 1004). A user in turn has a computing device configured to periodically check for messages from one or more of the pumps or from the server to determine whether any messages exist which would require action from that user.

The process 1000 terminates at an end operation 1008, which corresponds generally to completed delivery of at least one message or alarm to an appropriate set of individuals associated with that message or alarm.

FIG. 11 illustrates a pump-user communication system 1100 in which the targeted alarm and message handling can be implemented, according to a possible embodiment of the present disclosure. The pump-user communication system 1100 operates within a medical device network, such as the example network described above in conjunction with FIG. 6. The pump-user communication system 1100 illustrates an example of some of the various possible user groups connecting to a medical infusion pump 1102 that is associated with and delivering fluids to a patient 1104. The medical infusion pump 1102 can be any of a number of types of medical infusion pumps described above in conjunction with FIGS. 1-9.

The medical infusion pump 1102 is communicatively connected to a variety of computing devices 1106*a-e*, such as a pager 1106*a*, a personal data assistant 1106*b*, a cellular telephone 1106*c*, or a portable or desktop computing system 1106*d-e* associated with a variety of users 1108*a-e*. Each of the devices 1106*a-e* generally can communicate with the medical infusion pump 1102 via at least one communication method, such as by wired or wireless communication through one or more intermediate computing systems.

The users 1108a-e can include, for example, a primary physician 1108a, an on-call physician 1108b or other physician designated to respond to issues arising from medical infusion pumps, nurses 1108c, pharmacists 1108d, or other clinicians 1108e. Each of these users may be assigned to different types of messages generated at the medical infusion pump. For example, generalized notification alarms or reprogramming indicators can be targeted toward nurses who can respond easily to lower-priority messages. Or, a message indicating low or no fluid remaining for delivery is sent to a pharmacist (as well as a treating physician and nurse) to allow the pharmacist to provide additional fluids (e.g. drugs) for delivery via the medical infusion pump, optionally with physician approval. In another example, repeated messages corresponding to patient bolus events (i.e. the patient administering boluses to increase fluid delivery) indicate that the prescribed delivery rate is too low; the messages are routed to the primary physician 1108a for assessment and adjustment of the fluid delivery rate to the extent necessary. In a further example, emergency event messages (e.g. the pump has stopped or the patient requires immediate assistance) are routed to nurses 1108c that are currently working, as well as to the on-call physician 1108b.

In certain embodiments, more than one individual user or group of users may be notified of a message generated by the medical infusion pump 1102. In one possible embodiment, the group of users notified includes all of the users allowed to log in to the medical infusion pump directly (e.g. using the keypad of the pump or a computing system interfaced thereto). In further embodiments, specific individuals can be targeted for individualized messages by the pump based on the message generated by the pump. For example, the occurrence of a low fluid warning may require a nurse to check the status of the pump, but may require a pharmacist to obtain a new fluid supply (e.g. drug cartridge or bag) and install that new fluid supply for use with the pump. Each of these individuals can be sent specific messages, generated by the medical infusion pump or a computing system, relating to the message or alarm generated in the pump and possible corrective action needed.

2. Variable Intensity Alarms

Figure 12:
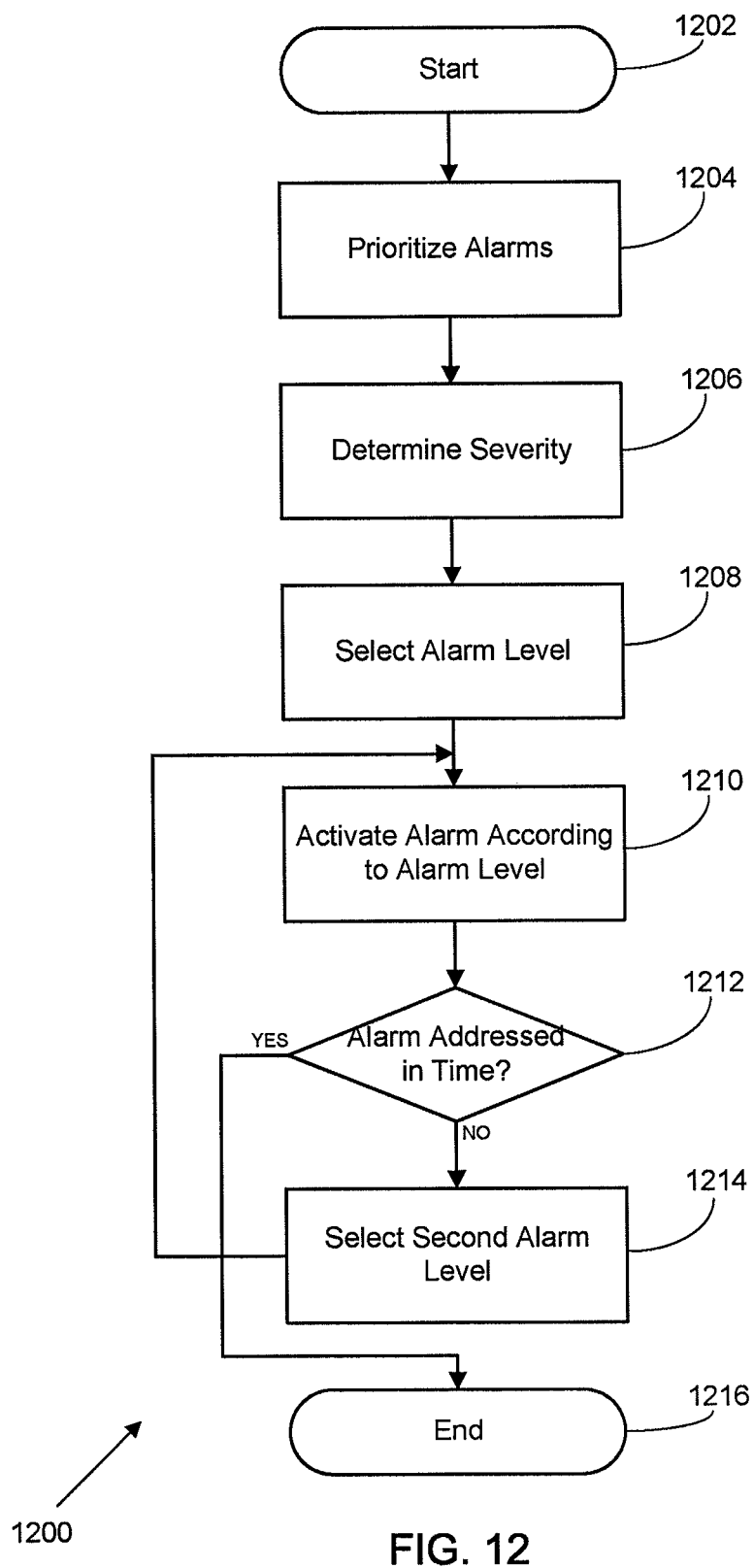
FIG. 12 illustrates a flowchart of methods and systems for providing variable intensity alarms in a medical infusion pump, according to a possible embodiment of the present disclosure.

FIG. 12 illustrates a flowchart of a process 1200 for providing variable intensity alarms in a medical infusion pump, according to a possible embodiment of the present disclosure. The process 1200 can be implemented in one or more pump application programs operable on a medical infusion pump, such as is described above in conjunction with FIGS. 1 and 4. The process 1200 allows alarms to be distributed at varying intensity levels depending upon the priority assigned to the alarm event. Priority may be based on a variety of factors, such as the severity of the alarm, the duration of the alarm, the time of day, and other events. Alarm events can include any of a number of events of differing importance. For example, informational alarm events and messages may trigger low priority alarm events, while pump faults, battery warnings, or damage warnings may correspond to higher priority alarm events. Other events, such as low fluid warnings, correspond to intermediate priority alarm events. The process 1200 is instantiated at a start operation 1202 which corresponds to initial operation of a medical infusion pump within a medical care network.

A prioritization module 1204 prioritizes alarms that can occur within a medical infusion pump. The prioritization module 1204 assigns a priority to the alarm, which generally reflects the speed with which the alarm must be responded to. In certain embodiments, the priority of an alarm can be dictated by the severity of the condition related to the alarm; in other embodiments, the priority of the alarm can change depending upon the duration of the alarm, the significance of the alarm event, the time of day, or other factors.

The prioritization module 1204 optionally allows a user to assign custom priorities to each alarm that can possibly be generated by a medical infusion pump. In certain embodiments, this corresponds to allowing users having access to settings of a medical infusion pump to edit a message or alarm severity listing in a user association data record, such as the record shown in FIG. 8, above. In further embodiments, user editing is accomplished by accessing severity settings in the pump from a remote system. In still other embodiments, the alarm severity settings are stored in a computing system remote from the pump, and user editing requires accessing a record, such as the user association data record, stored on that computing system. Other embodiments are possible as well.

In some embodiments, the prioritization module 1204 allows a user to assign one or more target groups to various alarms and alarm priorities in the medical infusion pump. The target groups correspond to one or more individuals who can be associated with an alarm or alarm level (i.e. severity or intensity), to ensure that those individuals are notified in the case that those certain alarms occur in the pump. For example, a user may associate a technician with a pump failure event, because a technician is likely required in the event that the pump fails during operation. Certain important patient events (e.g. pump programming anomalies) may require intervention by a treating physician; therefore, the medical infusion pump or a computing system communicatively connected to the pump can transmit a targeted alarm message to that physician. This optionally can occur in conjunction with the medical infusion pump outputting an audible or other type of alarm as well.

In further embodiments, the prioritization module 1204 allows the user to set themes relating to alarm events. The themes can include a mixture of visual, audible, and data communications alarms that can execute upon the occurrence of an alarm event. The themes can be arranged based on a time of day, with a nighttime theme configured to reduce the volume of the audible alarm to prevent awakening of other patients (e.g. patients in adjacent rooms in a medical care facility). The themes can also be arranged based on the general alarm type and the response type that is expected. For example, a theme can relate to maintenance, which may alert nurses and technicians of an issue with the medical infusion pump. Another theme could relate to drug delivery, and alerts nurses, doctors, and pharmacists of low drug supply warnings. Other themes can be implemented using the prioritization module 1204 as well.

A determine severity module 1206 executes upon each instance of an alarm event occurring in a medical infusion pump. The determine severity module 1206 generally corresponds to determining the type of alarm occurring in the medical infusion pump, and accessing a record of severity levels to find the severity level assigned to the current alarm event. Various alarm levels may be assigned to an alarm event in accordance with the present disclosure. In certain embodiments, such as embodiments using a user association data record of FIG. 8, three alarm levels are assigned: a high alarm level, a medium alarm level, and a low alarm level. Additional alarm levels may occur as well, based on the particular implementation of alarm levels used.

In certain embodiments, the determine severity module 1206 is configured to select an overall severity where two or more alarm events are occurring concurrently. For example, if a high severity event (e.g. pump malfunction) occurs concurrently with a low severity event (e.g. a message), the high severity event will be prioritized over the low severity event.

An alarm level selection module 1208 selects a specific alarm level for the alarm occurring in the medical infusion pump. The alarm level corresponds generally to the number of individuals targeted by an alarm, with more individuals targeted by alarms assigned a higher alarm level. Alarm levels are generally proportionate to the alarm severity for the alarm event with which it is associated. Therefore, higher severity alarms are output at a higher intensity, i.e., are intended to be perceived by more individuals than alarms output at lower intensity/lower severity. Alarm levels can correspond to different intensity settings of a variety of observable indicators, including sounds (specific sounds as well as sound volumes, pitch, and sound duration), target locations, target individuals, and color schemes. Other observable indicators could be used and varied in intensity as well.

In an example embodiment, alarm levels vary based on the volume and duty cycle of an alarm. In such an embodiment, a low alarm level corresponds to a low volume beep or other sound at a short, repeated duration or duty cycle. A high alarm level corresponds to a high volume beep or other sound at a longer, repeated duration or duty cycle. A medium alarm level exists at a setting between the low and high alarm levels (e.g. based on volume, duration, etc). Through use of varied alarm levels, more or fewer individuals will likely be alerted, based on the intensity, volume, or other varied intensity alarm.

An alarm activation module 1210 activates an alarm in accordance with the specific alarm level selected by the alarm level selection module 1208. The alarm activation module 1210 can cause output of a sound or communication of a message targeted to one or more people, with the number of people targeted increasing with increasing severity of the alarm event or increasing intensity of the alarm level.

The alarm activation module 1210 preferably executes within the medical infusion pump, outputting an alarm that is audible or visible to those in proximity to the pump. In certain embodiments, the alarm activation module 1210 also communicates the alarm to one or more computing devices, sound output devices, or displays remote from the medical infusion pump, for alerting additional individuals remote from the pump that action or intervention is needed at the pump. In further embodiments, selection of differing alarm levels causes the alarm activation module to communicate the alarm to more or fewer computing devices remote from the pump, with a higher alarm intensity corresponding to communication to a larger number of computing systems.

For example, the alarm activation module 1210 can output alarm events to one or more target groups of individuals, either within audible range or the pump or through communication of the alarm to a remote computing system. The target groups in audible range can include healthcare providers within a close proximity to the medical infusion pump, or a patient associated with the pump. Those outside of audible range who may require separate alarm transmission include, for example, nurses attending to the patient, doctors attending to the patient; pharmacists providing fluidic drugs administered by the medical infusion pump; or technicians required to repair the pump.

Operational flow proceeds from the alarm activation module 1210 to an alarm response assessment operation 1212. The alarm response assessment operation 1212 determines whether the alarm event associated with the alarm (i.e. the reason for the alarm to be triggered) remains in existence after a set period of time elapses. For example, the alarm response assessment operation 1212 can determine that an alarm event has not been rectified or acknowledged by a healthcare provider, or that the alarm event has not corrected itself within the pump (e.g. a pump error causing a pump reset) within a minute or a few minutes after the alarm event first occurs.

In certain embodiments, the amount of time allowed to elapse before operation of the alarm response assessment operation 1212 can be varied, and is user-programmable using menu screens available on the medical infusion pump. In further embodiments, a default amount of time is used.

If the alarm response assessment operation 1212 determines that the alarm event has not been addressed (i.e. the alarm event continues to exist), operational flow branches "no" to a second alarm level selection module 1214. The second alarm level selection module 1214 selects a second alarm level different from the first alarm level.

Preferably, the second alarm level selection module 1214 selects an alarm level at a higher intensity than the previous alarm level. For example, if the initial alarm level is set to a "low" alarm level, the second alarm level selection module 1214 preferably selects a "medium" or "high" alarm level, resulting in a higher intensity alarm output for alarms that are not addressed within the predetermined amount of time at the previous alarm level (before operation of the alarm response assessment operation 1212).

Operational flow from the second alarm level selection module 1214 returns to the alarm activation module 1210, causing the alarm to activate in accordance with the second alarm level selected by the second alarm level selection module 1214.

If the alarm response assessment operation 1212 determines that the alarm event no longer exists, operational flow branches "yes" to an end operation 1216. The end operation 1216 corresponds to completion or resolution of the alarm event in a medical infusion pump and ceasing of alarm activation in the pump. The end operation 1216 generally corresponds to a return to normal (non-alarming) operation of the medical infusion pump.

Through use of the process 1200, alarms can be output at a variety of initial intensities, or variable initial intensities based on a number of external and internal factors (as selected, for example, in the determine severity module 1206 and the alarm level selection module 1208). The process also provides for variable (preferably increasing) alarm intensities based on non-responsiveness to an alarm output at an initial alarm level.

In a possible embodiment of the process 1200, the alarm activation module 1210 first outputs only a communicated message to a nurse or other healthcare provider. After a period of time, the medical infusion pump can determine that the alarm condition has not yet been addressed; at that point, a local audible alarm can be activated as well, notifying those in proximity to the pump that an alarm condition exists. This example can correspond to the nighttime theme discussed above, in which local audible alarms are delayed or minimized in volume to the extent possible. Other themes and examples are possible as well, including a combination of communicated messages, audible alarms, visual alarms, or other alarm configurations.

3. Cost Tracking

Figure 13:
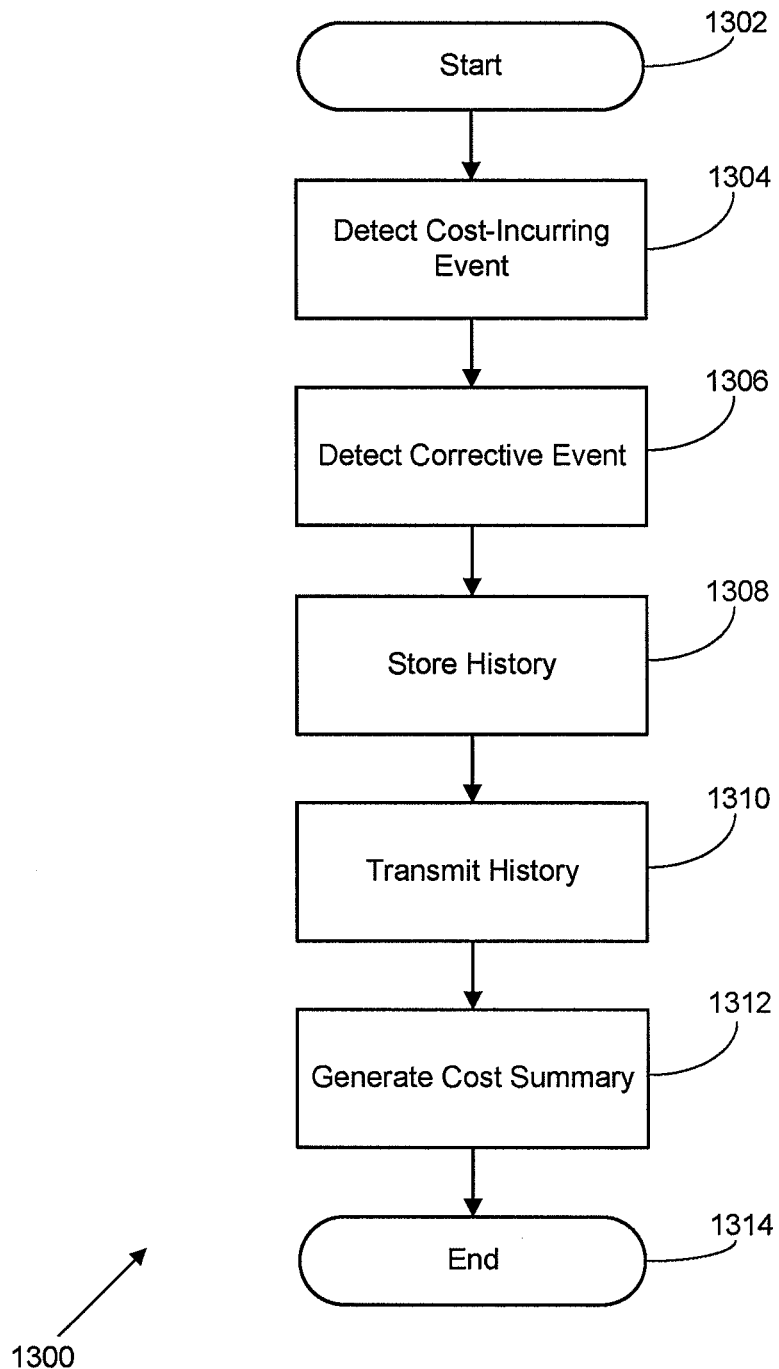
FIG. 13 illustrates a flowchart of methods and systems for cost tracking in a medical infusion pump, according to a possible embodiment of the present disclosure.

Referring now to FIG. 13 a flowchart of a process 1300 for cost tracking in a medical infusion pump is shown, according to a possible embodiment of the present disclosure. The cost tracking process 1300 provides detection and storage capabilities relating to cost-incurring events which occur in a medical infusion pump, such as use of a fluidic drug, a drug supply, an infusion set, a battery, or other disposable components used in conjunction with a medical infusion pump. By detecting and storing cost-incurring events in the medical infusion pump, cost administration in a healthcare facility is simplified and centralized. The cost tracking process 1300 can be used by a single medical infusion pump or a number of medical infusion pumps operating within a medical care network, such as the network shown in FIGS. 2 and 6.

The cost tracking process 1300 is instantiated at a start operation 1302, which corresponds to initial association of a medical infusion pump with a patient. An event detection module 1304 detects various events occurring in a medical infusion pump that may incur costs. Cost-incurring events are typically physical or structural events, such as usage of disposable devices (infusion sets, batteries, etc., cassettes, other disposables), drugs or other fluids, and overall time of operation of the medical infusion pump.

An optional corrective event detection module 1306 operates concurrently with the event detection module 1304, and detects corrective actions in the medical infusion pump. Corrective events are typically physical or structural events corresponding to events that, based upon their occurrence, may indicate the existence of a quality of care issue occurring with respect to the medical infusion pump, patient, or caregiver. Example corrective events include pump program cancellations, short-duration adjustments to pump settings, or occurrences where the medical infusion pump reaches one or more soft or hard limits set for fluid delivery. Pump program cancellations are events where a pump program is started and stopped in quick succession; a pump program cancellation may indicate that the pump was incorrectly programmed. Short-duration adjustments to pump settings can include events such as repeated bolus requests from a user, and may indicate that the overall pump program is not appropriate for the patient (e.g. a higher dosage may be needed). Occurrences where the medical infusion pump reaches soft or hard limits, or some duration in which that occurs, may also indicate a malfunction or improper programming of the pump.

A storage module 1308 stores cost-incurring and corrective events in a memory of the medical infusion pump. In a possible embodiment, the storage module 1308 maintains an event log representing the history of events occurring in the medical infusion pump. The event log can store a variety of information about the cost-incurring event or the corrective event, such as the time at which it occurred, the type of event, the specific event. Other information, such as the name of the current patient, the logged-in user, a pump identifier, and possible corrective action can be logged as well. An example event log is shown in FIG. 7, above.

A transmission module 1310 transmits all or a portion of the data stored in the event log to a computing system external to the medical infusion pump. The transmission module 1310 transmits the selected data via a communication interface, such as are described above in conjunction with the infusion pump network of FIG. 1 or the medical care network of FIG. 6. In various embodiments, the transmission module 1310 can be executed periodically, can execute upon request from the external computing system, or can execute once treatment of a patient has completed. The external computing system can be a local computing system incorporated into an infusion pump network, as described in conjunction with FIG. 1. In other embodiments, the external computing system can be a healthcare data server, such as are described in FIGS. 2 and 6. In still other embodiments, the external computing system can be a system managed by an entity external to a healthcare facility, such as an insurance company or billing management company.

A summary module 1312 generates a summary of the cost-incurring events (and optional corrective events). The summary module 1312 can create an electronic total cost or itemized cost summary that can be used as at least a portion of a bill generated by a billing department of a healthcare facility, for transmission to a patient and/or an insurance company. An example of a cost summary is shown below in FIG. 14. Operational flow in the process terminates at end operation 1314, which corresponds to completed cost tracking with respect to a single patient's use of a medical infusion pump.

Using the process 1300 in conjunction with a large number of medical infusion pumps allows for centralized cost tracking and cost management of the various medical infusion pumps. The event logs from the various medical infusion pumps can be aggregated at a computing system for overall cost analysis and generating reports relating to one or more of the medical infusion pumps (across multiple patients), multiple patients, or to assess overall performance of a department or healthcare facility with respect to occurrences of corrective events.

Furthermore, the various modules described in the process 1300 can be reordered or executed at various times. For example, the transmission module 1310 can execute periodically in a variety of medical infusion pumps, regardless of other modules' execution flow, to aggregate event data for comparison and analysis.

In additional embodiments one or more of the modules can execute on a computing system remote from the medical infusion pump. For example, the summary module 1312 generally executes on a computing system remote from the medical infusion pump. In such an example, the data stored in the storage module 1308 can be output to a server for generating a cost summary for the patient and is combined with other data for the patient's total bill.

In still further embodiments, the transmission module transmits at least a portion of the history of cost-incurring events to a remote computing system associated with a healthcare professional, such as a treating physician or nurse managing treatment of the patient. This computing system can be remote from the medical infusion pump generating the cost-incurring event data, or remote from the healthcare facility at which the medical infusion pump is located.

Figure 14:
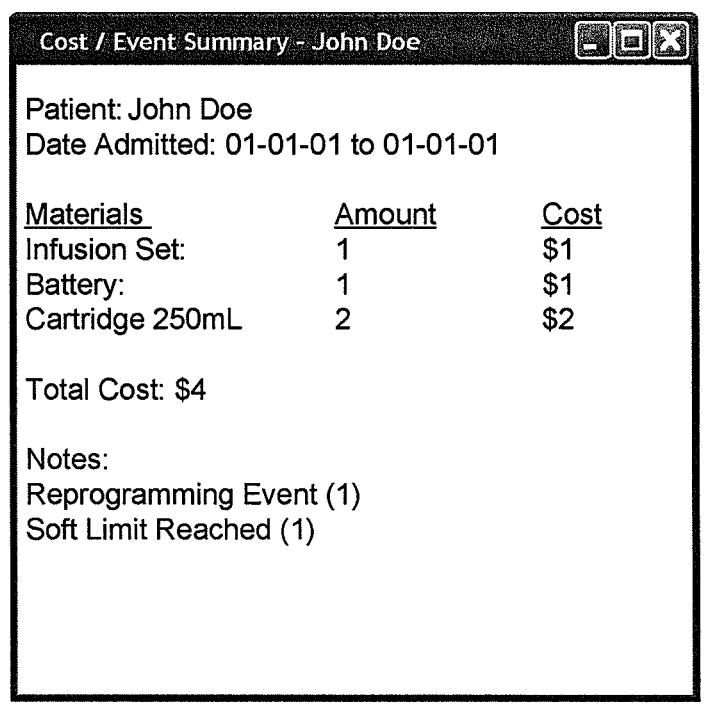
FIG. 14 illustrates an example cost summary window generated based on cost tracking data according to the methods and systems described in FIG. 13.

FIG. 14 illustrates an example cost summary window 1400 generated based on cost tracking data according to the methods and systems described in FIG. 13. The example cost summary window 1400 illustrates a sample summary report generated on a computing system based on execution of the summary module 1312 of FIG. 13. The example cost summary window 1400 illustrates a sample summary for the events shown in FIG. 7; however, other events and other configurations of the window 1400 are possible.

As shown in the cost summary window 1400, a cost summary can be generated for a particular patient and is based on events detected by the medical infusion pump. As shown in the current example, a patient "John Doe" was admitted to a medical care facility and used a medical infusion pump during one day, using an infusion set, a battery, and two fluidic drug cartridges. A total cost of each of these cost-incurring items is tallied. Additionally, notes relating to corrective events are logged and displayed in the window 1400, such as a reprogramming event or a soft limit reached, as described above in conjunction with FIG. 13.

Additional information can be gathered into a summary report beyond that which is shown in the cost summary window 1400. For example, information related to additional pumps and pump duration could be included, as well as additional information regarding the treatment prescribed to the patient.

4. Variable Delay for Sensing Downstream Pressure Decay

Referring now to FIGS. 15-20, systems and methods for implementing a variable delay in sensing downstream pressure decay is discussed, according to certain possible embodiments of the present disclosure. Generally, downstream pressure refers to pressure detected in a line of an infusion set (e.g. the line and needle delivering fluid to the patient). The systems and methods extend traditional functionality in a medical infusion pump immediately after a pump stroke. In the updated system, an occlusion alarm may not occur if some time elapses after the pump delivers fluids before the downstream pressure from the pump returns to an acceptable level. This may be preferable operation in the case where particularly thick fluidic drugs are delivered by the medical infusion pump, or some partial (but acceptable) occlusion of the infusion set occurs.

Figure 15:
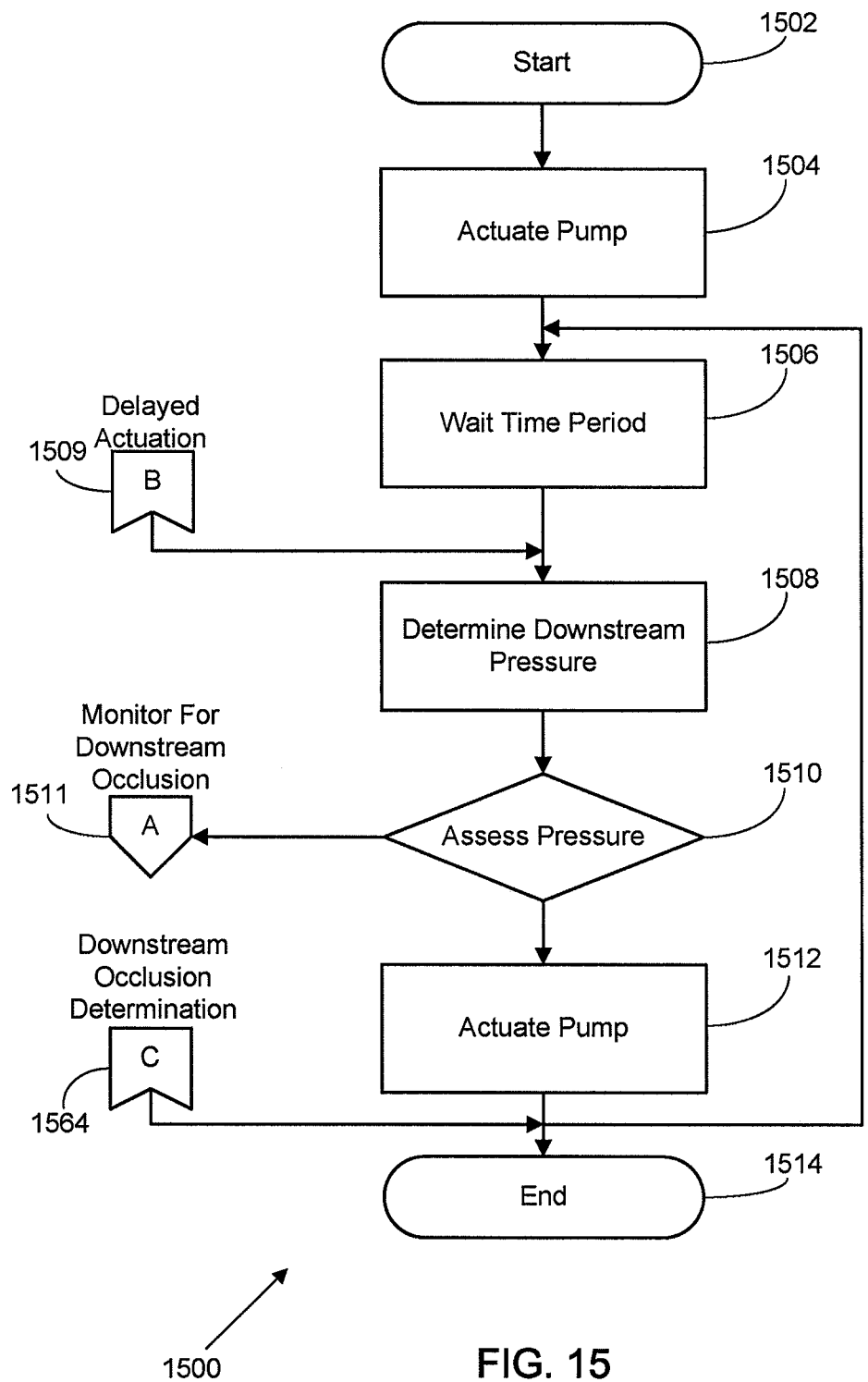
FIGS. 15-16 illustrate flowcharts of methods and systems for implementing a variable delay for sensing downstream pressure decay, according to a possible embodiment of the present disclosure.
Figure 16:
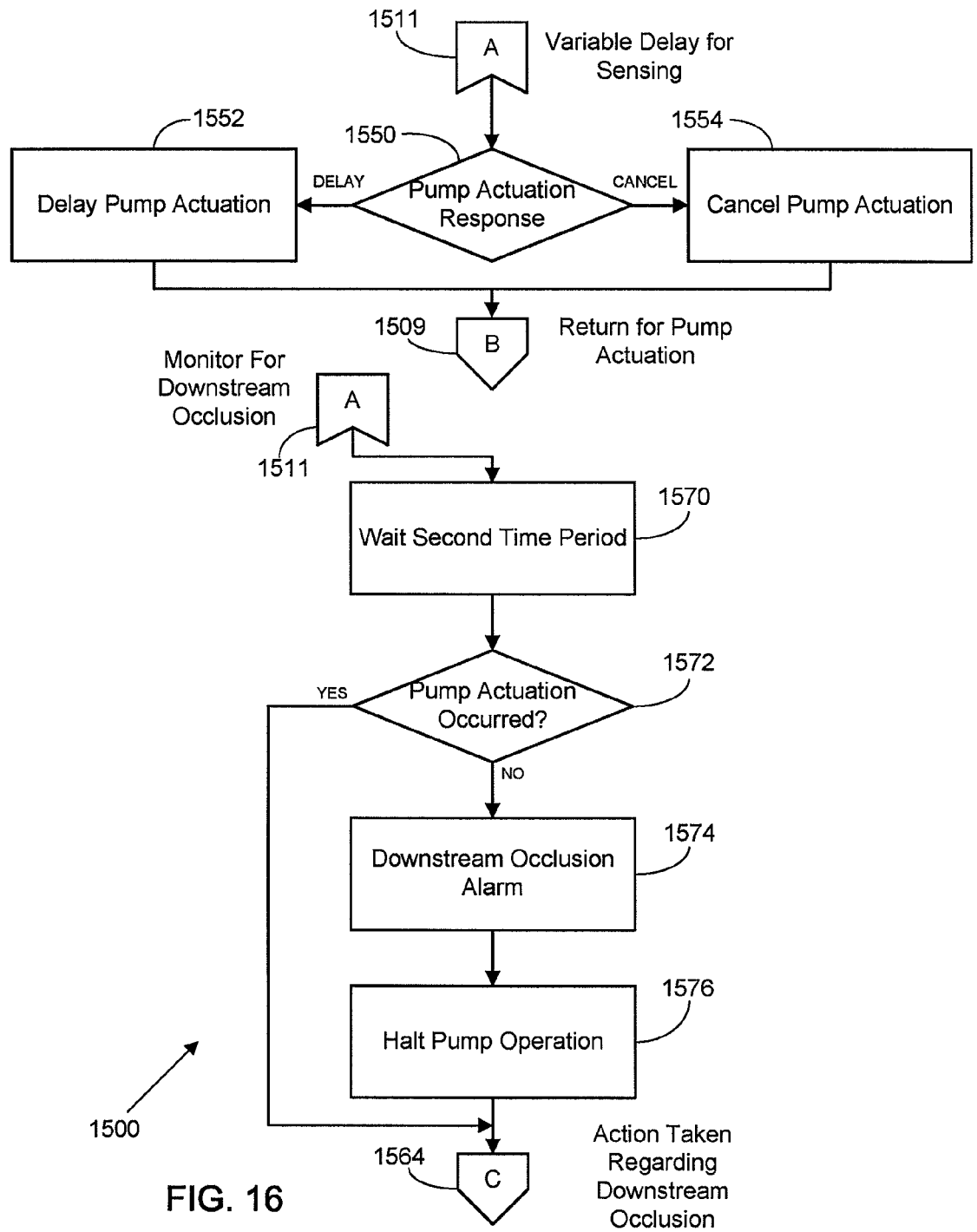

FIGS. 15-16 illustrate flowcharts of a process 1500 for implementing a variable delay for sensing downstream pressure decay, according to a possible embodiment of the present disclosure. The process 1500 allows the medical infusion pump to delay assessment of downstream pressure, and to delay subsequent delivery of fluids from the pump until the downstream pressure reaches an acceptable level.

Operational flow in the process 1500 is instantiated at a start operation 1502, which corresponds to initial operation of a medical infusion pump after selecting an option which enables variable delay in sensing downstream pressure decay. An actuation module 1504 initiates a pump stroke, causing delivery of a fluid to a patient through an infusion set connected downstream of the medical infusion pump. A wait module 1506 waits a predetermined time after actuation of the pump, delaying subsequent assessment of the status of the pump stroke actuated by the actuation module 1504.

The predetermined time of the delay caused by the wait module 1506 provides a period of time between pump strokes that results in an overall rate of drug or fluid delivery, as selected and programmed by a healthcare provider. A higher rate of fluid delivery results in a lower predetermined time delay by the wait module 1506, while a lower rate of drug delivery results in a higher delay.

A downstream pressure determination module 1508 determines the downstream pressure from the medical infusion pump. The downstream pressure determination module 1508 can use, for example, a downstream pressure sensor incorporated into the medical infusion pump which is configured to sense fluid pressure in a fluid set leading from the pump to a patient. Operational flow leading to the downstream pressure determination module 1508 comes from the wait module, as well as from off-page reference B 1509, which leads from a delayed earlier pump stroke, as described in FIG. 16.

Generally, pump strokes in a medical infusion pump occur at a predetermined rate to provide a reliable rate of fluid delivery to a patient. Such a consistent, predetermined rate could generally be accomplished in software through cycled operation of the actuation module 1504 (or 1512, below) and the wait module 1506; however, such a cycle must be interrupted for assessment of downstream pressure to ensure the safety of the patient. If the downstream pressure is too high, a downstream occlusion may have occurred, causing activation of a pump alarm. A pressure assessment operation 1510 then uses the downstream pressure determined using the downstream pressure determination module 1508 to assess whether a subsequent pump stroke should be allowed. The pressure assessment operation 1510 assesses the current pressure and compares that pressure to a threshold pressure.

If the pressure assessment operation 1510 determines that the pressure is not sufficiently below the predetermined threshold, such that a subsequent pump stroke would cause the downstream pressure to exceed that threshold, operational flow branches "delay" to off-page reference A 1511, which leads to a delayed actuation condition and initial monitoring for a downstream occlusion, as described below in conjunction with FIG. 16. In short, the system 1500 enters a waiting/assessment mode until the pressure drops to an accessible level, and the system monitors for a downstream occlusion, as described in FIG. 16.

If the pressure assessment operation 1510 determines that the pressure is sufficiently below a predetermined threshold that a subsequent pump stroke will not cause the downstream pressure to exceed that threshold (alternately, to not exceed the threshold by a substantial amount), operational flow branches "ok" to a second pump actuation module 1512. The second pump actuation module 1512 actuates the pump, causing the pump to deliver a pump stroke and deliver fluids to the patient again. Once the second pump actuation module 1512 occurs, operational flow can return to the wait module 1506 for further operation, cycling among the wait module, downstream pressure determination module 1508, pressure assessment operation 1510, and second pump actuation module 1512 to periodically deliver pump strokes of fluid to the patient until the prescribed amount of fluid is delivered, or a high downstream pressure is encountered, reaction to which is described in conjunction with FIG. 16. Once all fluids are delivered or a downstream occlusion is detected, operational flow can proceed to an end operation 1514, which corresponds with completed delivery of fluids to the patient. Off page reference C 1564, leading from FIG. 16, also leads to the end operation 1514.

Referring to FIG. 16, operational flow begins at off-page reference A 1511, leading from the pressure assessment operation 1510 in the case that the operation determines that the downstream pressure from the medical infusion pump is not sufficiently below the predetermined threshold, such that a subsequent pump stroke would cause the downstream pressure to exceed that threshold. From off-page reference A 1511, operational flow proceeds along two paths: a first path leads to a pump actuation response operation 1550, and a second path leads to an occlusion detection subsystem, via a second wait module 1570.

Figure 19:
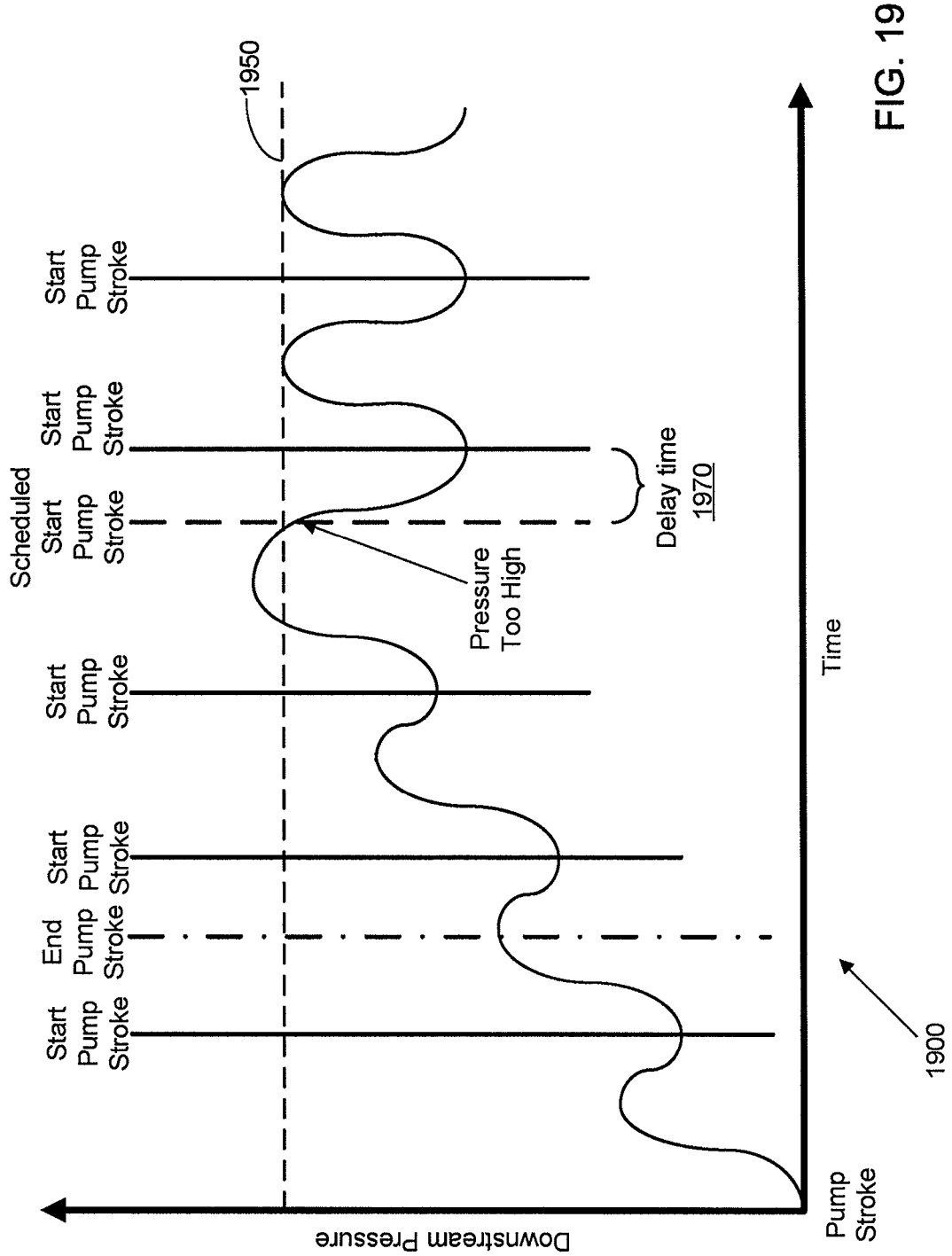
FIG. 19 illustrates an example graph of downstream pressure from a medical infusion pump using a variable delay for sensing downstream pressure decay, according to a possible embodiment of the present disclosure.
Figure 20:
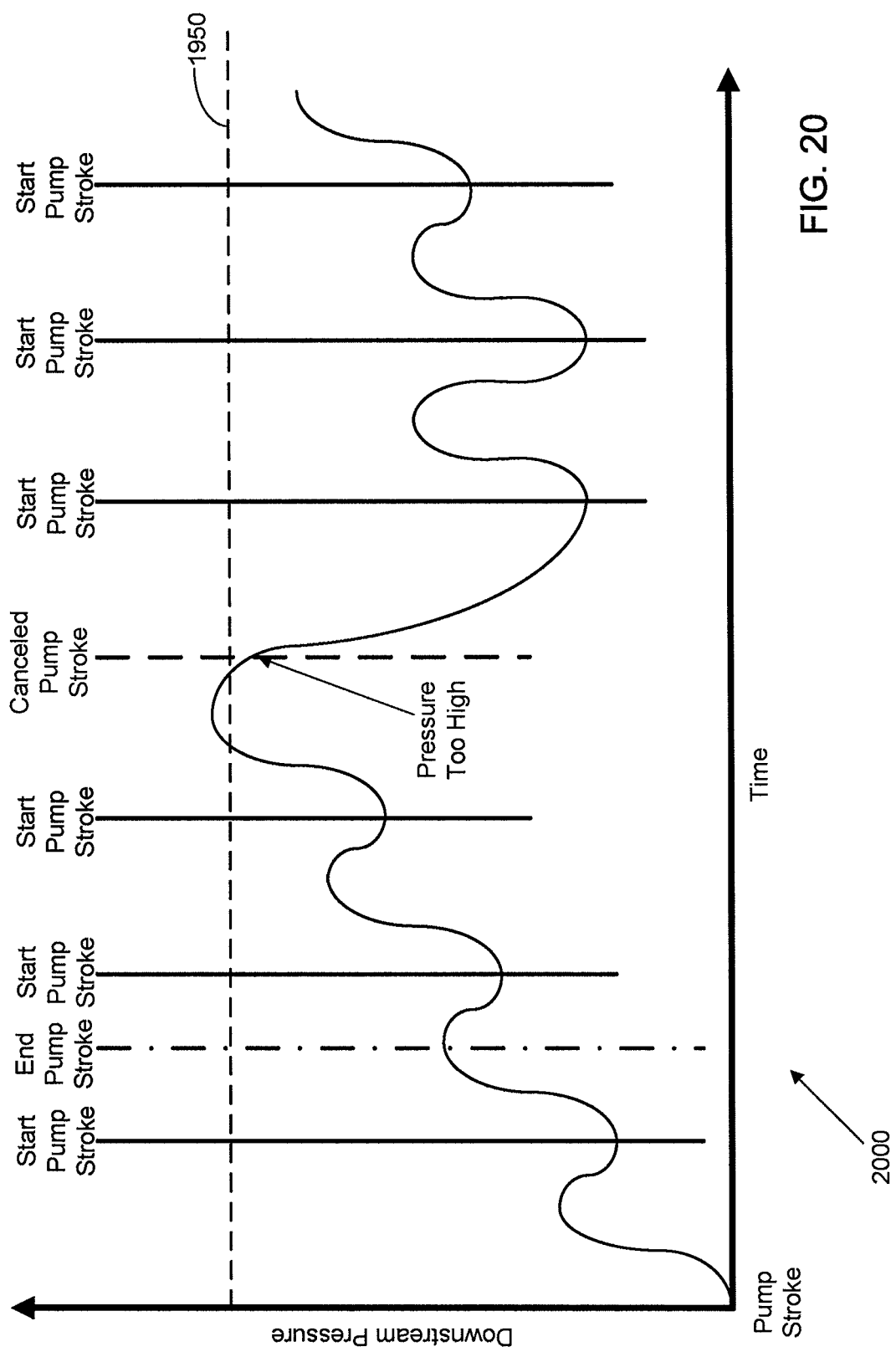
FIG. 20 illustrates a second example graph of downstream pressure from a medical infusion pump using a variable delay for sensing downstream pressure decay, according to a further possible embodiment of the present disclosure.

The pump actuation response operation 1550 determines a specific setting of the pump relating to how delayed pressure detection is accomplished. The pump can be set to respond to high pressure events in at least two ways. First, the pump may cancel later-scheduled pump strokes until the downstream pressure has decreased to a point where an additional pump stroke is safe to administer. Alternately, the pump may delay later-scheduled pump strokes until the downstream pressure has decreased to a safe point. Examples of operation in each of these two modes are shown in FIGS. 19-20.

If the pump actuation response operation 1550 is set to delay subsequent pump strokes, operational flow branches "delay" to a delay module 1552. If the pump actuation response operation 1550 is set to cancel a subsequent pump stroke, operational flow branches "cancel" to a cancel module 1554. The delay module 1552 delays the operation of the pump for a specified time, while the cancel module 1554 cancels the current pump actuation operation, allowing reassessment of downstream pressure at the time of the next scheduled pump stroke.

The specified time delayed by the delay module 1552 can vary according to the different possible implementations of the delay module. In a first example embodiment, the delay module 1552 delays a predetermined amount of time as programmed into the software systems installed onto the medical infusion pump. In a second example embodiment, the delay module 1552 delays a user-adjustable amount of time, with the user adjusting time periods for delay in a pump interface (e.g. the pump interface screens of FIG. 18). In a further embodiment, an adaptive time is used, where the medical infusion pump estimates a time delay based on the rate of pressure decay observed for one or more previous pump strokes.

From either the delay module 1552 or the cancel module 1554, operational flow proceeds to off page reference B 1555, which returns operation in the process 1500 to the downstream pressure determination module 1508 to determine whether, following the delay or cancellation of the pump stroke, an additional pump stroke can be administered, returning the process to normal (e.g. non-occluded) operation as described in conjunction with FIG. 15.

The wait module 1570 operates concurrently with the variable delay assessment portion of the process 1500 and waits a second period of time before allowing the system to determine whether a downstream occlusion exists. A pump actuation determination operation 1572 determines whether the pump has actuated since the pressure assessment operation 1510 determined that the pressure was too high to actuate the pump. If no pump actuation has occurred after the second time period set by the wait module 1570, operational flow branches "no" to a downstream occlusion alarm module 1574, which activates an alarm within the pump indicating the occurrence of a downstream occlusion. A halt pump operation module 1576 halts operation of the pump to ensure that no pump actuation takes place after the downstream occlusion is detected. Operational flow proceeds from the halt operation 1562 to an end operation 1514, of FIG. 15, through off-page reference C 1564.

In an alternative embodiment, an additional alarm can be incorporated in the medical infusion pump relating to the overall rate of fluid delivery. In such a case, that alarm may be activated in the pump prior to a downstream occlusion alarm if drug delivery is substantially slower than the programmed delivery rate (based on delayed or canceled pump strokes).

If a pump actuation has occurred after the second time period set by the wait module 1570, operational flow branches "yes" to the off-page reference C 1564. If the process 1500 has completed delivery of fluids at that point, operational flow proceeds to the end operation 1514. If the process has not yet completed delivery of fluids, operational flow returns to the system without halting the pump or activating the occlusion alarm, allowing continued fluid delivery.

Figure 17:
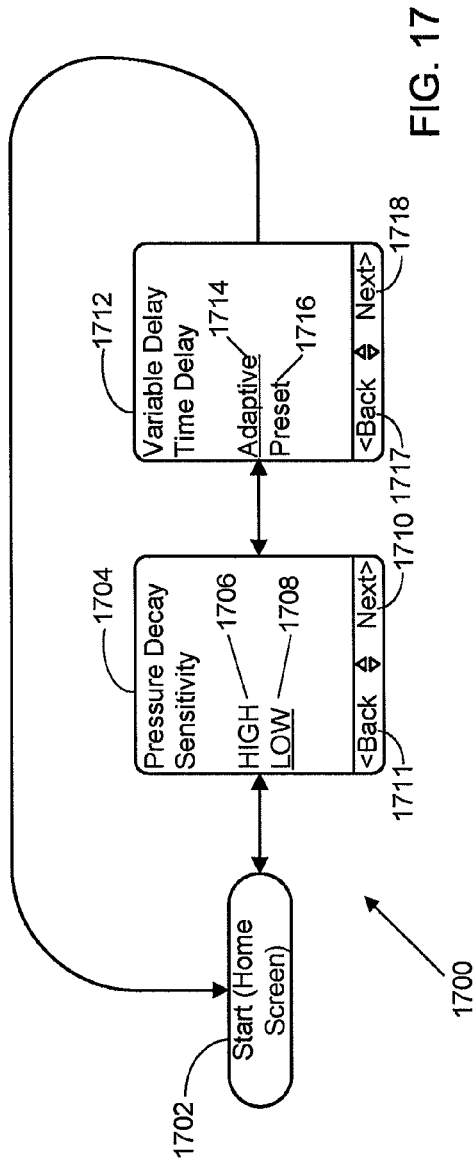
FIG. 17 illustrates a sequence of screens displayed on a medical infusion pump for activating a variable delay for sensing downstream pressure decay, according to a possible embodiment of the present disclosure.
Figure 18:
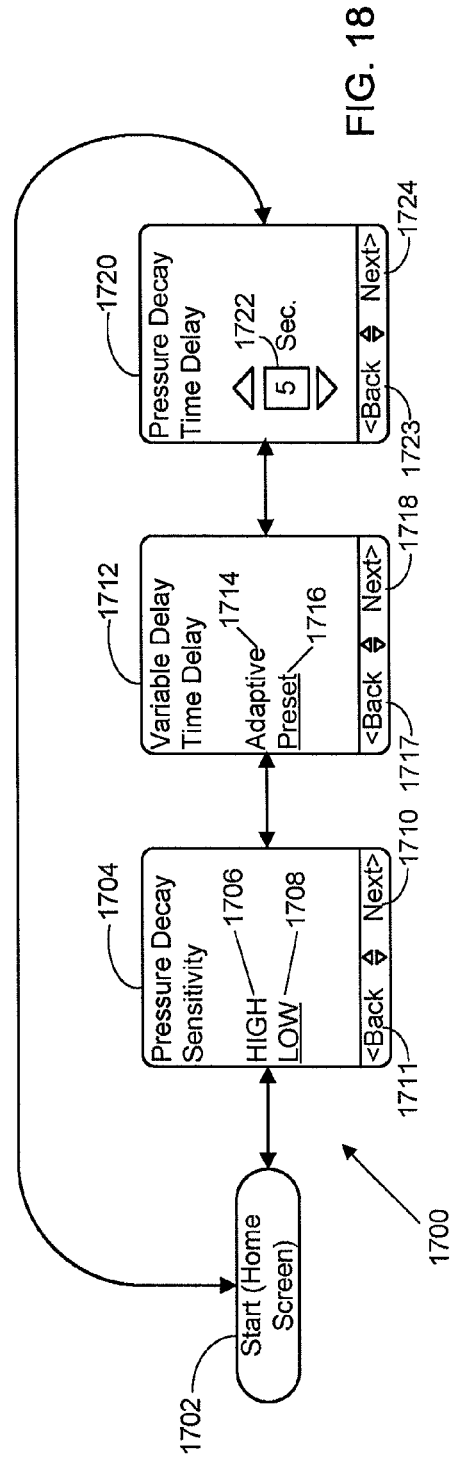
FIG. 18 illustrates a further sequence of screens displayed on a medical infusion pump for activating a variable delay for sensing downstream pressure decay, according to a further possible embodiment of the present disclosure.

FIGS. 17-18 illustrate two possible sequences of screens displayed on a medical infusion pump for activating a variable delay for sensing downstream pressure decay. FIG. 17 illustrates an example set of screens that would activate an adaptive downstream pressure decay monitoring system as described above in conjunction with FIG. 16. FIG. 18 illustrates an example set of screens that would activate a user-defined time period for monitoring downstream pressure decay.

In both FIG. 17 and FIG. 18, a user at a home screen 1702 can select to edit one or more options relating to pressure decay sensitivity. After the user selects to edit options relating to pressure decay sensitivity, operational flow transfers to a pressure decay sensitivity screen 1704. The pressure decay sensitivity screen 1704 allows the user to select between a high sensitivity setting 1706 and a low sensitivity setting 1708. The high sensitivity setting 1706 corresponds to a process of fluid delivery in which no delay is allowed prior to detection of occlusion, alarming, and suspension of fluid delivery. The low sensitivity setting 1708 corresponds to a process of fluid delivery in which some delay is allowed prior to detection of occlusion; one possible example of such a process is shown in FIGS. 15-16, above. If a user selects the low sensitivity setting and selects the next button 1710, operational flow within the pump causes focus on its screen to index to a variable time delay screen 1712. If the user selects the back button 1711, operational flow returns to the home screen 1702.

The variable time delay screen 1712 allows the user to select between an adaptive timing option 1714 and a preset timing option 1716. The adaptive timing operation corresponds to an adaptive delay in the variable delay for downstream pressure decay, as described in conjunction with FIG. 16. The preset timing option 1716 corresponds to allowing a user of the pump an ability to set the time for which the system will delay prior to checking downstream pressure to determine the advisability of a subsequent pump actuation command.

Relating to the variable time delay screen 1712, FIG. 17 illustrates selection of the adaptive timing option 1714 and selecting the next button 1718. In that case, operational flow returns to the home screen 1702, allowing the system to resume normal operation while using the systems for variable time delay for pressure decay, such as those described in FIGS. 15-16, above. Selecting the back button 1717 returns the user to the pressure decay sensitivity screen 1704.

FIG. 18 illustrates selection of the preset timing option 1716 and selecting the next button 1718. Operational flow indexes to a timing screen 1720, which includes a scroll box 1722 with which the user can cycle through to select a number of seconds for which the pump will delay prior to assessing its ability to actuate another pump stroke, in accordance with the systems of FIGS. 15-16. Once the correct time is selected by using the scroll box 1722 and soft keys displayed at the bottom of the screen (controlled, for example, by keypad 424 of FIG. 4), selection of the next button 1724 returns focus to the home screen 1702. Selection of the back button 1723 returns focus to the variable time delay screen 1712.

FIGS. 17-18 provide only example user interface sequences that may be implemented in a medical infusion pump. However, other options may be possible as well. For example, in an embodiment where a present user-inaccessible delay time is programmed into the pump, no timing screen 1720 may be necessary. Further, one or more additional options for determining a timing system for the variable delay of pressure decay system can be included in the system settings.

FIGS. 19-20 illustrate example graphs of downstream pressure from a medical infusion pump using a variable delay for sensing downstream pressure decay, according to certain embodiments of the present disclosure. FIG. 19 illustrates an example graph 1900 of downstream pressure for a system using a time delay for determining timing for a subsequent pump actuation, as described in conjunction with the delay module 1552 of FIG. 16. FIG. 20 illustrates an example graph 2000 of downstream pressure for a system using a pump stroke cancellation configuration for subsequent pump actuation, as described in conjunction with the cancel module 1554 of FIG. 16.

Both figures show periodic pump actuation, with the beginning of each pump stroke occurring approximately at the solid vertical lines passing through the base of each curve portion (i.e. about the local minimum) and the ending of the pump stroke approximately corresponding to apex of each curve portion (i.e. about the local maximum). The approximate end of the pump stroke is illustrated in the figures as the dotted-dashed vertical line in each figure; however not all pump stroke endings are shown for figure clarity. At the end of each pump stroke it is seen that pressure generally decays from the local maximum until the subsequent pump stroke is actuated.

A threshold pressure value 1950, illustrated in the figures by a horizontal dashed line, indicates a pressure above which the pump is configured to not operate. This may be because of regulatory concerns or limitations of the pump mechanism, the infusion set, or the patient receiving fluids. In general, the goal of the systems illustrated in FIGS. 15-20 is to maintain fluid delivery and ensure that the fluid delivery remains below the threshold value.

As can be seen in FIG. 19, the example pressure graph shows four pump strokes (one occurring on the axis, time=0) occurring prior to the downstream pressure from the pump exceeding the threshold pressure value 1950. Each of these four pump strokes are regularly spaced over time. However, when the time approaches for the fifth pump stroke to occur (denoted by the "Scheduled Start Pump Stroke" vertical dashed line), the medical infusion pump, using the software and hardware systems described in FIGS. 15-18, detects that the pressure is near the threshold pressure value, and therefore a subsequent pump stroke should not occur. This prevents the downstream pressure from significantly exceeding the threshold value. In certain embodiments, the system can be configured to delay pump strokes to ensure that the threshold pressure value 1950 is not exceeded by any pump stroke.

A time delay 1970 is introduced prior to allowing a subsequent pump stroke to occur. Determining the length of this time delay is a matter of design of the processes controlling actuation of pump strokes. In various embodiments, this time delay 1970 can be based on an adaptive time delay determination based on observation of rates of pressure decay for the previous pump strokes (e.g. one or more of strokes 1-4), or can be a preprogrammed or user-programmable delay time, as explained in conjunction with FIGS. 16 and 18. After the time delay 1970, the system will verify that the pressure has decreased sufficiently to ensure that a subsequent pump stroke will not exceed (or significantly exceed) the threshold value 1950. If the downstream pressure has decreased sufficiently, the medical infusion pump is allowed to actuate subsequent pump strokes.

FIG. 20 also shows four pump strokes occurring prior to the downstream pressure from the pump exceeding the threshold pressure value 1950. Again, each of these pump strokes are equally spaced to illustrate differences in operation between the embodiments of FIGS. 19 and 20. At the location of the scheduled fifth pump stroke (i.e. the same position as the "Scheduled Start Pump Stroke" of FIG. 19), illustrated by a vertical dashed line, the medical infusion pump determines that the downstream pressure following the scheduled pump stroke would exceed the threshold value. In the embodiment of FIG. 20, the scheduled fifth pump stroke is canceled, and pressure is reassessed at the next scheduled pump stroke time.

As shown, only one pump stroke is canceled before the downstream pressure decreases to the point that subsequent pump strokes are determined to be safe and are delivered. However, in the case of a slower-decreasing downstream pressure, additional pump strokes could be canceled by the system, to the extent that the canceled pump strokes would occur within a separate timeframe for alarming due to downstream occlusion.

5. Timed Intermittent Bolus by Pressure

Figure 21:
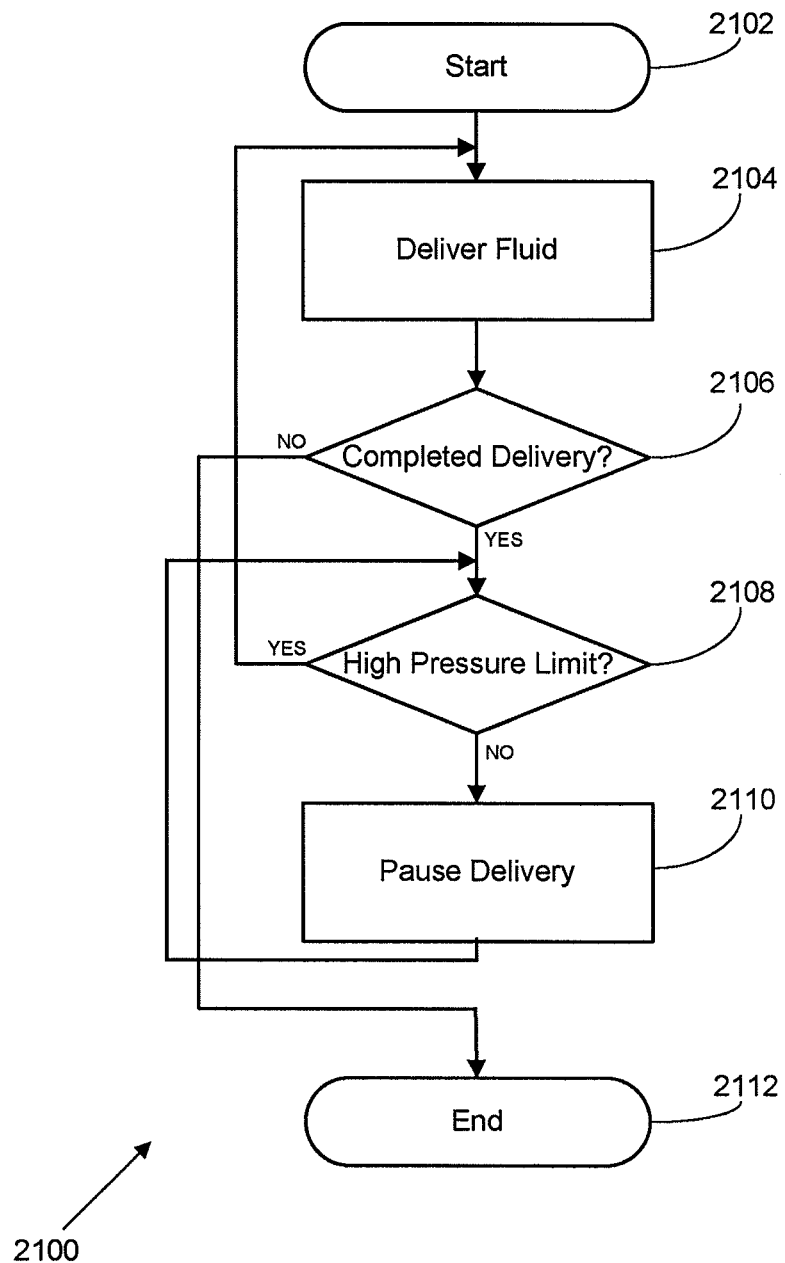
FIG. 21 illustrates a flowchart of methods and systems for delivering a timed intermittent bolus by pressure in a medical infusion pump, according to a possible embodiment of the present disclosure.
Figure 22:
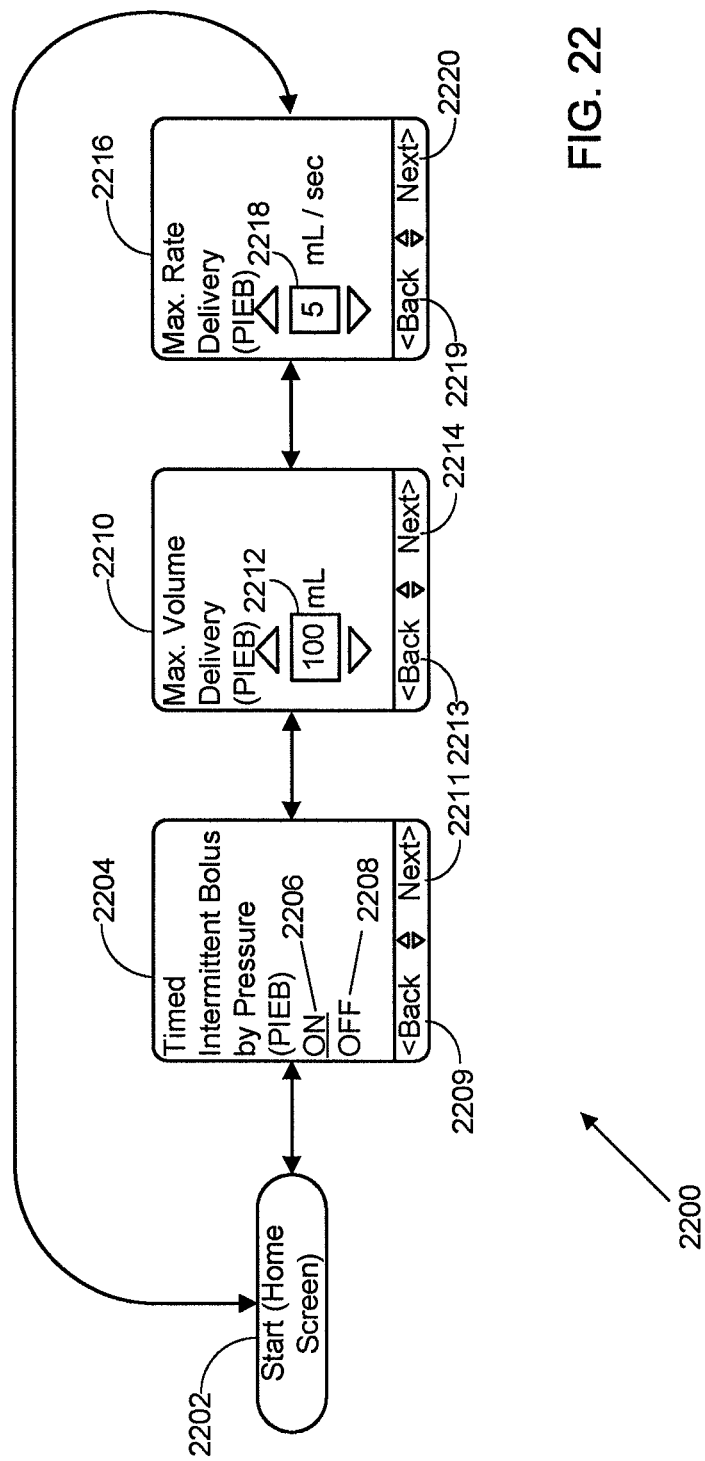
FIG. 22 illustrates a sequence of screens displayed on a medical infusion pump for activating a timed intermittent bolus by pressure, according to a further possible embodiment of the present disclosure.
Figure 23:
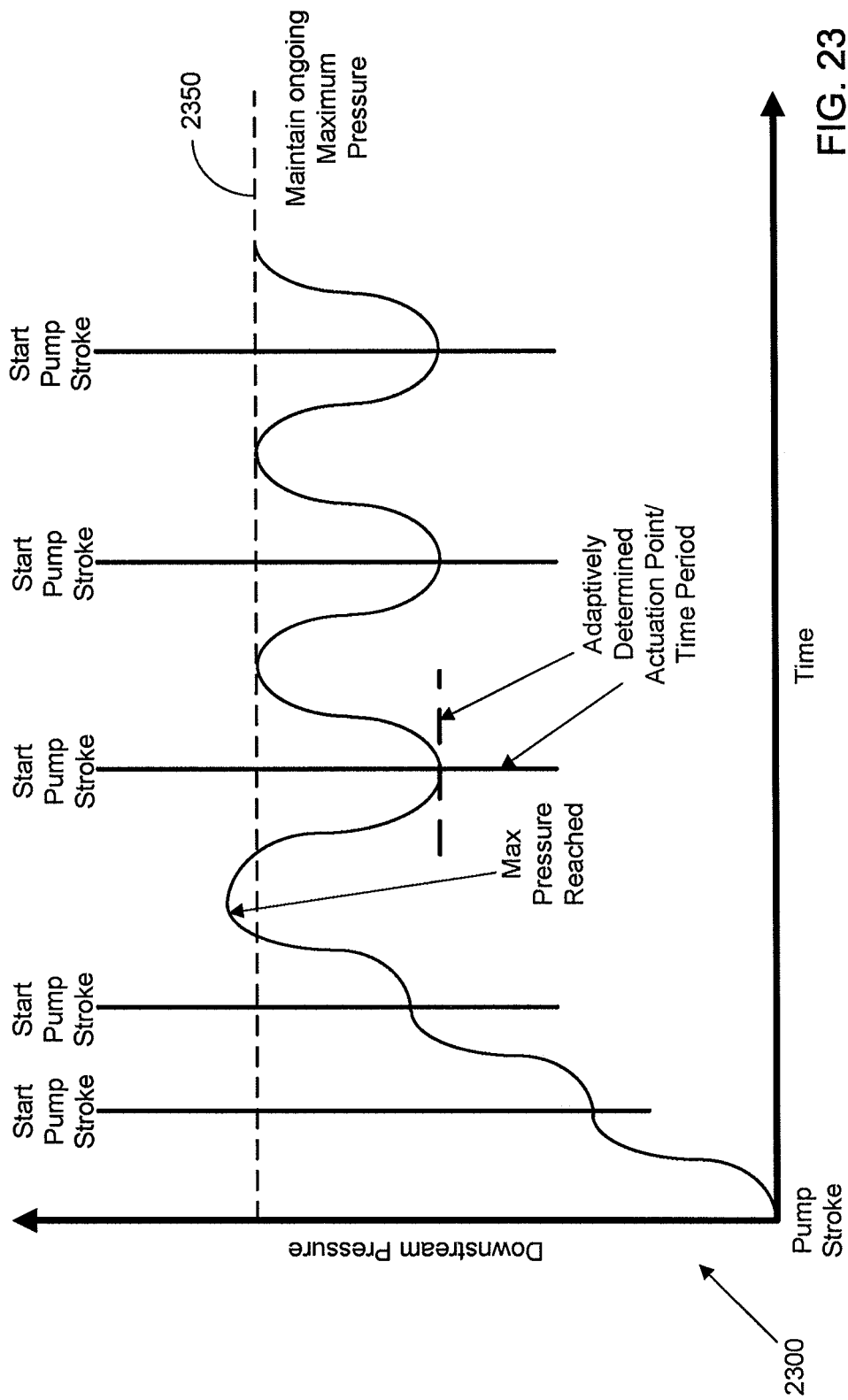
FIG. 23 illustrates an example graph of downstream pressure from a medical infusion pump delivering a timed intermittent bolus by pressure, according to a further possible embodiment of the present disclosure.

Referring now to FIGS. 21-23, a process for managing a timed intermittent bolus by pressure is shown, in accordance with certain embodiments of the present disclosure. The process for managing a timed intermittent bolus described herein is generally implemented as software and hardware in a medical infusion pump configured to actuate a pump mechanism (e.g. the pump mechanism described in FIG. 4, above) in a specific manner.

The timed intermittent bolus by pressure system described in the following figures generally allows the medical infusion pump to deliver fluids to a patient at a maximum rate by delivering consecutive pump strokes until a maximum pressure is reached. At that point, the system waits for a period of time, then actuates additional pump strokes. The timed intermittent bolus by pressure system can be used to deliver a predetermined amount of a fluid over a minimum time, or may be used to deliver a maximum amount of fluid over a set time.

FIG. 21 illustrates a flowchart of a process 2100 for delivering a timed intermittent bolus by pressure in a medical infusion pump. Operational flow is instantiated at a start operation 2102, which corresponds to initial programming of the medical infusion pump to deliver the timed intermittent bolus by pressure, such as by using the screen sequence of FIG. 22, below. Operational flow proceeds to a fluid delivery module 2104, which corresponds to actuating a pump stroke in the medical infusion pump.

A delivery completion operation 2106 assesses whether fluid delivery is completed according to the programmed timed bolus by pressure. In certain embodiments, delivery of fluids is programmed to complete upon delivery of a total amount of a fluid. In other embodiments, delivery completes upon delivery of a maximum amount of fluid over a programmed period of time. In still other embodiments, the condition under which the medical infusion pump completes operation is user-selectable, among the two options (total fluid or total time). If the delivery completion operation determines that delivery of fluids is complete, operational flow branches "yes" to the end operation 2112, described below. If the delivery completion operation 2106 determines that delivery of fluids is not yet complete, operational flow branches "no" to a high pressure limit determination operation.

The high pressure limit determination operation 2108 monitors the downstream pressure from the medical infusion pump to determine whether that pressure exceeds a threshold pressure or is sufficiently close to the threshold pressure that actuating the pump would exceed the threshold pressure. In certain embodiments, the high pressure limit determination operation 2108 determines whether the downstream pressure would exceed the threshold pressure by a substantial, predetermined amount.

If the high pressure limit determination operation 2108 determines that a subsequent pump stroke is safe to actuate (e.g. the downstream pressure that is detected is sufficiently low that a subsequent pump stroke actuation would not result in a downstream pressure in excess of the threshold pressure), operational flow returns to the fluid delivery module 2104. By cycling the fluid delivery module 2104, delivery completion operation 2106, and high pressure limit determination operation 2108, pump strokes are repeated until a high pressure threshold is reached or until fluid delivery is completed (e.g. within the specified time or up to the specified volume of fluid).

If the high pressure limit determination operation 2108 determines that a subsequent pump stroke is not safe to actuate (e.g. the downstream pressure that is detected is not sufficiently low, and that a subsequent pump stroke actuation would cause a downstream pressure in excess of the threshold pressure), operational flow proceeds to a pause module. The pause module 2110 pauses delivery of fluid from the medical infusion pump. The length of the pause may be determined in a number of different ways. In one embodiment, the pause module 2110 pauses adaptively, by observing a rate of downstream pressure decay and estimating a time at which the downstream pressure will be sufficiently low to allow actuation of a subsequent pump stroke. In a further embodiment, the pause module 2110 introduces a short pause, allowing the process 2100 to spin-wait using the pause module 2110 and the high pressure limit determination operation 2108, to periodically check the pressure for a specific level below the threshold at which pump actuation can restart. In a still further embodiment, the pause module is user-programmable to pause a specified length of time. Other embodiments are possible as well.

Operational flow returns from the pause module to the high pressure limit determination operation 2108, for reassessment of downstream pressure. The high pressure limit determination operation 2108 repeats operation to ensure that the downstream pressure is now sufficiently low to allow a subsequent pump stroke actuation via the fluid delivery module 2104. Operation within the process 2100 proceeds from the high pressure limit determination operation 2108 accordingly.

If the delivery completion operation 2106 determines that the preset amount of fluid has been delivered or that the preset time has elapsed in the system, operational flow branches "yes" to an end module 2112, which ceases operation of the timed intermittent bolus by pressure process 2100. Operation within the medical infusion pump can then cease or return to regular or previous operation.

FIG. 22 illustrates a sequence of screens 2200 displayed on a medical infusion pump for activating a timed intermittent bolus by pressure, according to a possible embodiment of the present disclosure. The sequence of screens 2200 leads a user through the process of initiating a timed intermittent bolus by pressure process, such as the process described in FIG. 21, above. The sequence of screens leads from a home screen 2202, which is a general screen included in the medical infusion pump that allows a user to select and program various pump delivery and display settings.

Upon user selection of a timed intermittent bolus by pressure option (not shown) in the home screen 2202, the medical infusion pump indexes focus on an enablement screen 2204. The enablement screen 2204 allows the user to enable or disable the timed intermittent bolus by pressure system. The enablement screen includes an on option 2206 and an off option 2208, selectable via the soft keys present on the medical infusion pump. A user selecting the on option 2206 and pressing the next option 2211 causes operational flow to index to a volume delivery screen 2210. The back option 2209 returns the user to the home screen 2202.

The volume delivery screen 2210 allows a user to set the maximum volume of fluid to be delivered through use of the timed intermittent bolus by pressure process, such as the process described in FIG. 21. The volume delivery screen 2210 includes a scroll box 2212 that allows a user to select a total volume delivery for fluids according to the timed intermittent bolus by pressure delivery methodology described, for example, in FIG. 21. A user can scroll through a range of values in the volume delivery screen. When the user has selected the desired volume, the user can select the next button 2214 to move to a rate delivery screen 2216. A back button 2213 returns the user to the enablement screen 2204.

The rate delivery screen 2216 allows a user to select a maximum delivery rate at which the fluid should be delivered. A scroll box 2218 present in the rate delivery screen 2216 allows the user to scroll through a range of delivery rate values to select an appropriate maximum rate. A next button 2220 confirms the user's selection of the maximum delivery rate and maximum volume, initiates delivery in accordance with the timed intermittent bolus by pressure systems described herein, and returns focus to the home screen 2202. A back button 2219 returns the user to the volume delivery screen 2210.

Optionally, additional screens can be added to the sequence 2200 as well. For example a screen could allow the user to select a total elapsed time for operation of the timed intermittent bolus by pressure operation. Or, a further screen could allow the user to adjust the threshold for downstream pressure. Other screens may be used as well.

FIG. 23 illustrates an example graph 2300 showing downstream pressure from a medical infusion pump delivering a timed intermittent bolus by pressure, according to a further possible embodiment of the present disclosure. In the embodiment shown, The figure shows variable-frequency pump actuation, with the beginning of each pump stroke occurring at the solid vertical lines passing through the local minimum of the pressure curve and the ending of the pump stroke approximately corresponding to apex of each curve portion (i.e. about the local maximum). The end of the pump stroke is not illustrated in the figure; however, for the first few pump strokes a subsequent pump stroke is initiated shortly after completion of the previous pump stroke. At the end of each pump stroke it is seen that pressure generally reaches approximately a local maximum until the subsequent pump stroke is actuated.

As shown in the example graph 2300, three pump strokes (one at the axis) cause the downstream pressure to exceed a set threshold 2350. At the end of each pump stroke, the downstream pressure is assessed to determine whether to allow the subsequent pump stroke. At the end of the three pump strokes, pump actuation pauses (e.g. using the pause module 2110 of FIG. 21) due to exceeding the threshold, and the medical infusion pump waits a period of time until the downstream pressure has decreased to a point sufficiently below the threshold 2350. As described in conjunction with FIG. 21, the medical infusion pump can wait an adaptive period of time, a user-defined period of time, or a constant, preprogrammed period of time before determining again whether to cause actuation of a pump mechanism again (once the pressure has sufficiently decreased). At that point, the system described will continue actuating the pump mechanism at approximately the point where the pressure has dropped from the preceding pump stroke to allow a safe subsequent pump stroke, thereby maintaining a high (but primarily below the threshold) downstream pressure for delivering fluid to a patient.

Additional examples of a pressure graph are possible as well. The threshold, pump stroke frequency, and pressure graph profiles described herein are intended as examples only, and are by no means intended to limit the scope of the present disclosure. Furthermore, although the various methods for waiting for re-actuation of a pump and for establishing a downstream pressure threshold are discussed, there may be other methods of performing the methods and systems described herein may be used as well, consistent with the present disclosure.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A method of assessing downstream pressure in a medical infusion pump, the method comprising:
   determining a downstream pressure at the end of a pump stroke in a medical infusion pump;
   waiting a time period;
   determining a downstream pressure at the end of the time period;
   assessing the downstream pressure at the end of the time period, wherein the time period is adaptively determined at the end of each pump stroke based on a rate of decrease of downstream pressure from the medical infusion pump after one or more previous pump strokes; and
   based on the assessing step, selectively actuating a subsequent pump stroke.

2. The method of claim 1, wherein waiting a time period includes monitoring the downstream pressure over the time period.

3. The method of claim 1, wherein assessing the downstream pressure at the end of the time period includes determining that the downstream pressure is below a maximum downstream pressure by at least a threshold amount.

4. The method of claim 1, further comprising, upon elapsing of a second time period in the absence of a pump stroke, triggering a downstream occlusion detection alarm.

5. A medical infusion pump configured for management of fluid pressure decay, the medical infusion pump comprising:
   a pump mechanism configured to deliver fluids to a patient;
   a memory;
   a programmable circuit arranged to control the pump mechanism and operatively connected to the memory, the programmable circuit programmed to:
      determine a downstream pressure while the pump mechanism is operating;
      wait a time period;
      determine a downstream pressure at the end of the time period, wherein the time period is adaptively determined based on a rate of decrease of downstream pressure from the medical infusion pump based on previous operation of the pump mechanism;
      assess the downstream pressure at the end of the time period; and
      based on the assessment, selectively delivering more fluid via the pump mechanism.

6. The medical infusion pump of claim 5, wherein waiting a time period includes monitoring the downstream pressure over the time period.

7. The medical infusion pump of claim 5, wherein the programmable circuit is further programmed to, upon determining the downstream pressure is below a maximum downstream pressure by at least a threshold amount, delivering additional fluid.

8. The medical infusion pump of claim 5, wherein the programmable circuit is further programmed to, upon determining that the downstream pressure is not below a maximum downstream pressure by at least a threshold amount, delaying a subsequent pump stroke at least until the downstream pressure is below a maximum downstream pressure by the threshold amount.

9. The medical infusion pump of claim 5, wherein the programmable circuit is further programmed to, upon determining that the downstream pressure is not below a maximum downstream pressure by at least a threshold amount, cancelling a subsequent pump stroke.

10. A method of delivering a fluid from a medical infusion pump, the method comprising:
    pumping fluid from the medical infusion pump;
    determining that a subsequent pump stroke will cause a downstream pressure to exceed a high pressure limit;
    upon determining that a subsequent pump stroke will cause the downstream pressure to exceed the high pressure limit, pausing delivery of fluid for a time period; and
    upon elapsing of the time period, rechecking the downstream pressure to determine whether it remains within a threshold of the high pressure limit that will result in a subsequent pump stroke causing the downstream pressure to exceed the high pressure limit.

11. The method of claim 10, further comprising, upon determining whether the downstream pressure remains within a predetermined threshold of the high pressure limit, pausing pumping of fluid for a second time period.

12. The method of claim 10, wherein the time period is adaptively determined by a rate of decrease of pressure downstream of the medical infusion pump.

13. The method of claim 12, wherein the time period is adaptively determined by a rate of decrease of pressure downstream of the medical infusion pump during a preceding pump stroke.

14. The method of claim 12, wherein the time period is adaptively determined by a rate of decrease of pressure downstream of the medical infusion pump during a preceding number of pump strokes.

15. The method of claim 10, wherein the predetermined time period is user-adjustable.

16. The method of claim 10, wherein the medical infusion pump delivers a maximum volume of fluid over a minimized length of time.

17. The method of claim 10, further comprising pausing issuance of an occlusion alarm upon determining that a subsequent pump stroke will cause the downstream pressure to exceed the high pressure limit.

18. A medical infusion pump comprising:
    a pump mechanism;
    a memory;
    a programmable circuit arranged to control the pump mechanism and operatively connected to the memory, the programmable circuit programmed to:
       deliver fluid via the pump mechanism until it is determined that a subsequent pump stroke will cause a downstream pressure to exceed a high pressure limit;
       upon determining that a subsequent pump stroke will cause the downstream pressure to exceed the high pressure limit, pause delivery of fluid via the pump mechanism for a time period; and
       upon elapsing of the time period rechecking the downstream pressure to determine whether it remains within a threshold of the high pressure limit that will result in a subsequent pump stroke causing the downstream pressure to exceed the high pressure limit.

19. The pump of claim 18, wherein the pump mechanism delivers one or more pump strokes to deliver fluid.

20. The pump of claim 18, wherein the time period is adaptively determined by a rate of decrease of pressure downstream of the medical infusion pump during a preceding pump stroke.

21. The pump of claim 18, wherein the time period is adjustable based on settings stored in the memory.

22. The pump of claim 19, wherein the medical infusion pump delivers a maximum volume of fluid over a minimized length of time.

23. The system of claim 18, wherein the programmable circuit is further programmed to pause issuance of an occlusion alarm upon determining that a subsequent pump stroke will cause the downstream pressure to exceed the high limit.

24. A method of delivering a fluid from a medical infusion pump, the method comprising:
    initiating a pump mechanism for delivering fluid from the medical infusion pump until it is determined that a subsequent pump stroke will cause a downstream pressure to exceed a high pressure limit;
    upon determining that a subsequent pump stroke will cause the downstream pressure to exceed the high pressure limit, pausing delivery of fluid for a time period;
    upon elapsing of the time period, rechecking the downstream pressure to determine whether it remains within a threshold of the high pressure limit that will result in a subsequent pump stroke causing the downstream pressure to exceed the high pressure limit; and
    if the downstream pressure is outside of the threshold, initiating the pump mechanism for delivering additional fluid from the medical infusion pump;
    wherein the medical infusion pump delivers a maximum volume of fluid over a minimized length of time.

25. The method of claim 24, further comprising, if the downstream pressure remains within the threshold of the high pressure limit, pausing delivery of fluid for a second time period.

26. The method of claim 24, wherein the time period is adjustable based on settings stored in the memory.

27. A method of generating alarms in a medical infusion pump, the method comprising:
    determining a severity level of an alarm based on an alarm event, an alarm event corresponding to a condition that indicates the need for an alarm;
    selecting an alarm level from among a plurality of alarm levels, the alarm level selected based on the severity of the alarm and an alarm level criteria, each alarm level corresponding to at least one of a plurality of different predefined target groups to be notified by the alarm; and
    activating the alarm in accordance with the selected alarm level.

28. The method of claim 27, further comprising:
    maintaining activation of the alarm for a predetermined time;
    if the alarm event is not addressed during the predetermined time, selecting a second alarm level from among the plurality of alarm levels; and
    activating the alarm in accordance with the second alarm level.

29. The method of claim 28, wherein the second alarm level corresponds to a target group that is a superset of a target group associated with the alarm level.

30. The method of claim 27, wherein the alarm levels are selected from a range of settings consisting of:
    alarm volumes;
    alarm sounds;
    alarm duty cycle;
    alarm target locations; and
    color schemes.

31. The method of claim 27, wherein the alarm level criteria are selected from the group consisting of:
    duration of the alarm event;
    significance of the alarm event; and
    time of day.

32. The method of claim 27, wherein alarm events are selected from a group consisting of:
    informational alarm events;
    high importance alarm events;
    pump faults;
    battery warnings;
    low fluid warnings;
    damage warnings; and
    messages.

33. The method of claim 27, wherein target groups are selected from a group consisting of:
    healthcare providers within a close proximity to the medical infusion pump;
    a patient associated with the medical infusion pump;
    nurses attending to the patient;
    doctors attending to the patient;
    pharmacists providing fluidic drugs administered by the medical infusion pump;
    and technicians.

34. The method of claim 27, further comprising prioritizing one or more alarm events based on a severity of each alarm event.

35. A medical infusion pump comprising:
    a pump mechanism;
    a memory;
    a programmable circuit arranged to control the pump mechanism and operatively connected to the memory, the programmable circuit programmed to:
        determine a severity level of an alarm based on an alarm event, an alarm event corresponding to a condition that indicates the need for an alarm;
        select an alarm level from among a plurality of alarm levels, the alarm level selected based on the severity of the alarm and an alarm level criteria, each alarm level corresponding to at least one of a plurality a different predefined target groups to be notified by the alarm; and
        activate the alarm in accordance with the selected alarm level.

36. The medical infusion pump of claim 35, wherein the alarm events are selected from a group consisting of:
    informational alarm events;
    high importance alarm events;
    pump faults;
    battery warnings;
    low fluid warnings;
    damage warnings; and
    messages.

37. The medical infusion pump of claim 35, wherein the programmable circuit is further programmed to allow a user to associate an alarm event with one or more alarm levels.

38. The medical infusion pump of claim 35, wherein the programmable circuit is further programmed to allow a user to associate an alarm event with a target group.

39. The medical infusion pump of claim 35, wherein the programmable circuit is further programmed to allow a user to associate an alarm level with one or more target groups.

40. The medical infusion pump of claim 35, wherein the programmable circuit is further programmed to allow a user to define one or more themes, each theme associating one or more alarm events with corresponding alarm levels.

41. The medical infusion pump of claim 35, wherein the programmable circuit is further programmed to prioritize one or more alarm events based on a severity of each alarm event.

42. The medical infusion pump of claim 35, wherein the alarm levels are selected from a range of settings consisting of:
- alarm volumes;
- alarm sounds;
- alarm duty cycle;
- alarm target locations; and
- color schemes.

43. The medical infusion pump of claim 35, wherein target groups are selected from a group consisting of:
- healthcare providers within a close proximity to the medical infusion pump;
- a patient associated with the medical infusion pump;
- nurses attending to the patient;
- doctors attending to the patient;
- pharmacists providing fluidic drugs administered by the medical infusion pump; and
- technicians.

44. A method of generating alarms in a medical infusion pump, the method comprising:
- determining a severity level of an alarm based on an alarm event, an alarm event corresponding to a condition that indicates the need for an alarm;
- selecting an alarm level from among a plurality of alarm levels, the alarm level selected based on the severity of the alarm and an alarm level criteria, each alarm level corresponding to at least one of a plurality of different predefined target groups to be notified by the alarm;
- activating the alarm in accordance with the selected alarm level;
- maintaining activation of the alarm for a predetermined time;
- if the alarm event is not addressed during the predetermined time, selecting a second alarm level from among the plurality of alarm levels; and
- activating the alarm in accordance with the second alarm level.

45. The method of claim 44, wherein the alarm levels are selected from a range of settings consisting of:
- alarm volumes;
- alarm sounds;
- alarm duty cycle;
- alarm target locations; and
- color schemes.

46. The method of claim 44, wherein target groups are selected from a group consisting of:
- healthcare providers within a close proximity to the medical infusion pump;
- a patient associated with the medical infusion pump;
- nurses attending to the patient;
- doctors attending to the patient;
- pharmacists providing fluidic drugs administered by the medical infusion pump; and
- technicians.

47. A method of assessing downstream pressure in a medical infusion pump, the method comprising:
- determining a downstream pressure at the end of a pump stroke in a medical infusion pump;
- waiting a time period;
- determining a downstream pressure at the end of the time period;
- assessing the downstream pressure at the end of the time period wherein the time period is user adjustable; and
- selectively actuating a subsequent pump stroke based on the assessed downstream pressure.

48. A method of delivering a fluid from a medical infusion pump, the method comprising:
- pumping fluid from the medical infusion pump until a downstream pressure reaches a high pressure limit;
- upon reaching the high pressure limit, pausing delivery of fluid for a time period; and
- upon elapsing of the time period, rechecking the downstream pressure to determine whether it remains within a threshold of the high pressure limit.

49. The method of claim 48, further comprising pausing issuance of an occlusion alarm upon reaching the high pressure limit.

50. The method of claim 49, wherein if the downstream pressure remains within a threshold of the high pressure limit after rechecking the downstream pressure the occlusion alarm is issued.

51. The method of claim 48, further comprising, upon determining whether the downstream pressure remains within a predetermined threshold of the high pressure limit, pausing pumping of fluid for a second time period.

52. The method of claim 48, wherein the time period is adaptively determined by a rate of decrease of pressure downstream of the medical infusion pump.

53. The method of claim 52, wherein the time period is adaptively determined by a rate of decrease of pressure downstream of the medical infusion pump during a preceding pump stroke.

54. The method of claim 52, wherein the time period is adaptively determined by a rate of decrease of pressure downstream of the medical infusion pump during a preceding number of pump strokes.

55. The method of claim 48, wherein the predetermined time period is user-adjustable.

56. The method of claim 48, wherein the medical infusion pump delivers a maximum volume of fluid over a minimized length of time.

57. A medical infusion pump comprising:
- a pump mechanism;
- a memory;
- a programmable circuit arranged to control the pump mechanism and operatively connected to the memory, the programmable circuit programmed to:
  - deliver fluid via the pump mechanism until a downstream pressure reaches a high pressure limit;
  - upon reaching the high pressure limit, pause delivery of fluid via the pump mechanism for a time period; and
  - upon elapsing of the time period rechecking the downstream pressure to determine whether it remains within a threshold of the high pressure limit.

58. The pump of claim 57, wherein the programmable circuit is further programmed to pause issuance of an occlusion alarm upon reaching the high pressure limit.

59. The pump of claim 58, wherein the programmable circuit is further programmed to issue the occlusion alarm if the downstream pressure remains within the threshold of the high pressure limit when the downstream pressure is rechecked.

60. The pump of claim 57, wherein the pump mechanism delivers one or more pump strokes to deliver fluid.

61. The pump of claim 57, wherein the time period is adaptively determined by a rate of decrease of pressure downstream of the medical infusion pump during a preceding pump stroke.

62. The pump of claim 57, wherein the time period is adjustable based on settings stored in the memory.

63. The pump of claim 57, wherein the medical infusion pump delivers a maximum volume of fluid over a minimized length of time.

* * * * *